United States Patent
Inomata et al.

(10) Patent No.: US 6,642,375 B2
(45) Date of Patent: Nov. 4, 2003

(54) FLUORESCENT SUBSTANCES

(75) Inventors: Hiroko Inomata, Saitama (JP); Hiroshi Shinoki, Saitama (JP); Masayoshi Kojima, Saitama (JP); Yukio Sudo, Saitama (JP); Junji Nishigaki, Kanagawa (JP); Osamu Seshimoto, Saitama (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 09/731,279

(22) Filed: Dec. 6, 2000

(65) Prior Publication Data

US 2003/0013088 A1 Jan. 16, 2003

(51) Int. Cl.$^7$ .................. C07H 19/04; C07H 15/00; C12Q 1/68; C07D 293/00
(52) U.S. Cl. .................. 536/26.6; 435/6; 435/91.1; 536/4.1; 536/17.2; 536/17.4; 536/18.1; 536/4; 530/300; 530/331; 548/100; 548/146; 548/300.1; 548/311.7; 548/333.5
(58) Field of Search .................. 435/6, 91.1; 536/4.1, 536/17.2, 17.4, 18.1, 4, 26.6; 530/300, 331; 548/100, 146, 300.1, 311.7, 333.5

(56) References Cited

U.S. PATENT DOCUMENTS

| | | | |
|---|---|---|---|
| 5,486,616 A | 1/1996 | Waggoner et al. | 548/217 |
| 5,986,086 A | 11/1999 | Brush et al. | 536/26.26 |

FOREIGN PATENT DOCUMENTS

WO   WO 01/21624   3/2001

OTHER PUBLICATIONS

Usagawa et al, " Cynanine Dye And Light–Absorbing Composition Containing It", Jun. 21, 1991, pp 521–529.*

(List continued on next page.)

*Primary Examiner*—Jezia Riley
(74) *Attorney, Agent, or Firm*—Reed Smith LLP

(57) ABSTRACT

The present invention provides a fluorescent substance which is represented by a formula: A-B-C
wherein
A is a residue of natural or synthetic nucleotide, oligonucleotide, polynucleotide, or derivative thereof, and binds to B at a base moiety in said residue, or A is a residue of avidin or streptavidin;
B is a divalent linking group or a single bond; and
C is a monovalent group derived from a general formula (I) and binds to B at a reactive group present in $R^1$ or $R^2$:

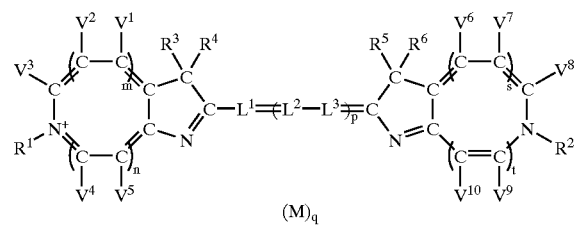

wherein $R^1$ and $R^2$ each independently represent an alkyl group that may be substituted with a reactive group capable of covalently bonding to A-B-; $R^3$, $R^4$, $R^5$, and $R^6$ each independently represent an alkyl group, and $R^3$ and $R^4$, and/or $R^5$ and $R^6$ may bind to each other to form a saturated carbon-ring together with a carbon atom(s) to which they bind; $V^1$, $V^2$, $V^3$, $V^4$, $V^5$, $V^6$, $V^7$, $V^8$, $V^9$ and $V^{10}$ each independently represent a hydrogen atom or a monovalent substituent, and two adjacent groups thereof may bind to form a ring; $L^1$, $L^2$, and $L^3$ represent a substituted or unsubstituted methine group; each of m, n, s, and t represents 0 or 1, provided that m+n=1 and s+t=1; p represents 1, 2, or 3; M represents a counter ion; and q represents a number required to neutralize the charge of a molecule. The fluorescent substance of the present invention is useful as a labeling substance for nucleic acids, or as a reagent for analyzing biological components such as nucleic acids, proteins or sugars.

16 Claims, 1 Drawing Sheet

OTHER PUBLICATIONS

Przhonskaya et al, "Photo–Induced Proton Transfer In Polymethine Dye Solutions", pp. 54–60 (Jun. 2002).*

"Gene Characterization Kits", Stratagene Catalog, pp39 (1988).*

Matthews et al, "Analytical Strategies for the Use of DNA Probes", Analytical Biochemistry, vol. 169, pp. 1–25 (1988).*

Robert et al., "Localization of Subunits of Transcription Factors IIE and IIF Immediately Upstream . . . Major Late Promoter", The Journal of Bio. Chem, vol. 271, No. 15, pp. 8517–8520 (1996).*

Mikhailenko et al., "Fluorescence and Lasing of Nonequilibrium Protolytic Forms of Polymethine Dye Molecules," *Soviet Journal of Quantum Electronics*, vol. 7, No. 3, pp. 322–324 (1980).

* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthesized

<400> SEQUENCE: 1
tggccgcctt caacgctcag                                               20

<210> SEQ ID NO 2
<211> LENGTH: 26
<212> TYPE: DNA
<213> ORGANISM: Artificial Sequence
<220> FEATURE:
<223> OTHER INFORMATION: Synthesized

<400> SEQUENCE: 2
tcaggcactt tcattaacag gcacat                                        26

FLUORESCENT SUBSTANCES

FIELD OF THE INVENTION

The present invention relates to a fluorescent substance using azamethine compounds which are useful as fluorescent labeling reagents and to its use. More particularly, the present invention relates to fluorescent nucleotides and fluorescent avidin using azamethine compounds, and uses thereof.

BACKGROUND OF THE INVENTION

One of the most frequently used molecular biological techniques for detecting homologous nucleic acid sequences is DNA/DNA, RNA/RNA or RNA/DNA hybridization. In this technique, nucleic acid (DNA or RNA) used as a probe is labeled, and the labeled nucleic acid is hybridized to a nucleic acid (DNA or RNA) to be detected. When the nucleic acid used as a probe has a homology to the nucleic acid to be detected, each single-stranded nucleic acid hybridizes to its complementary sequence so as to form a double-stranded sequence, and then the double-stranded sequence is detected by a label of the probe.

Conventionally, when nucleic acid is used as a probe, a technique of labeling the probe with radioisotope has been employed and the presence of hybridization between the probe and a target nucleic acid has been detected using autoradiography.

Although the techniques using radioisotopes for labeling a gene probe is especially superior in its high sensitivity, there exist such problems that the handling of radioisotopes is complicated because safety of the laboratory must be ensured and special care must be taken in the disposal of radioactive wastes. Moreover, radioisotopes can be used only for a limited time because they have a half-life period.

Therefore, non-radioactive labeling techniques have been developed as more simple techniques. For example, techniques of labeling a gene probe with biotin molecules (European Patent No. 0 063 879) or with digoxigenin molecules (European Patent Application No. 0 324 474 A1) are known. After hybridization of a labeled nucleic acid probe to the nucleic acid sequence to be detected, biotin molecules or digoxigenin molecules are present in the resulting double-stranded nucleic acid. After hybridization, binding of (strept)avidin-marker enzyme complex or anti-digoxigenin antibody-marker enzyme complex to the resultant double-stranded nucleic acid sequence allows detection of nucleic acids to which the probes was hybridized. However, such detection methods using enzymes are disadvantageous in terms of sensitivity and specificity.

Other than the above techniques, various techniques of labeling a target substance with fluorescent dye have been studied. For example, a desired fluorescent labeling reagent (1) possesses a high fluorescent quantum yield, (2) possesses a high molecular extinction coefficient, (3) is water-soluble and does not self-quench by agglutinating in an aqueous solvent, (4) is not susceptible to hydrolysis, (5) does not photo-dissociate easily, (6) is not susceptible to background fluorescence, and (7) has a previously introduced reactive substituent which forms covalent bonding with a target substance.

Fluorescein isothiocyanate (FITC) and rhodamine isothiocyanate, which are well-known as fluorescent labeling reagents, possess high fluorescent quantum yields, but have drawbacks such that the molecular extinction coefficients is low and the excitation and luminous wavelength is 500 nm to 600 nm and therefore these reagents are susceptible to the influence of background fluorescence of a membrane used for blotting.

As dyes having a high molecular extinction coefficient, polymethine dyes are known such as cyanine dye described in U.S. Pat. No. 5,486,616, Japanese Patent Application Laid-Open Nos. 2-191674, 5-287209, 5-287266, 8-47400, 9-127115, 7-145148 and 6-222059, and barbiturate oxonol described in Journal of Fluorescence, 5, 231, 1995. However, there exist some problems such that they are almost insoluble in water and if they are dissolved, hydrolysis occurs. Also, strong intermolecular interactions between dyes can cause formation of aggregates in an aqueous medium so that self-quenching of fluorescence is often observed.

Moreover, cyanine dyes described in Japanese Patent Application Laid Open No. 2-191674 and the like are superior dyes because they have water-solubility due to introduction of a sulfonic acid group into a relatively stable chromophore and the formation of aggregates is prevented. However, its fluorescent quantum yield is not sufficiently high and synthesis of the dye is difficult due to the introduction of a sulfonic acid group. Under such circumstances, it has been required to develop a fluorescent dye which has a strong fluorescence as well as a high water-solubility and stability enough to cause no quenching of fluorescence due to aggregation.

Another example of a frame dye with high fluorescence intensity is azaindoleninecyanin dye described in GB Patent No. 870,753. However, applicability of this azaindoleninecyanin dye as a fluorescent labeling reagent remains unknown because in this patent application, there is no description as to essential features of a fluorescent labeling reagent, such as water-solubility, cohesiveness and solution stability, and there is no examples of introduction of a reactive substituent which causes covalent bonding with a target substance. Moreover, examples of application of azaindoleninecyanin to photographic use are shown in Japanese Patent Application Laid Open Nos. 4-358143, 3-135553, 1-280750 and European Patent No. 341958. These examples utilize absorbance characteristics of azaindoleninecyanin, but do not focused its luminescent characteristics and do not positively utilize it.

SUMMARY OF THE INVENTION

The object to be solved by the invention is to overcome the abovementioned problems of the conventional techniques. The object to be solved by the present invention is to provide a novel fluorescent nucleotide which is useful in labeling nucleic acid, and a novel fluorescent avidin which is useful in analyzing biological components such as nucleic acids, proteins or sugars.

Having conducted intensive study to solve the above described problems, the present inventors formed a complex of a nucleotide and a recently developed fluorescent labeling reagent, i.e. an azamethine compound, and labeled and detected nucleic acids using this complex. As a result, the inventors have found that the complex is superior in the ratio of uptake into nucleic acids and the fluorescent intensity in the detection. Furthermore, the present inventors formed a conjugate of a streptavidin and an azamethine compound, and detected biotin-labeled nucleic acids using the conjugate. As a result, the inventors found that the fluorescence is detected in an intensity which depends on the level of nucleic acid. The present invention has been completed on the basis of these findings.

According to the present invention, there is provided a fluorescent substance which is represented by a formula: A-B-C
wherein
A is a residue of natural or synthetic nucleotide, oligonucleotide, polynucleotide, or derivative thereof, and binds to B at a base moiety in said residue, or A is a residue of avidin or streptavidin;
B is a divalent linking group or a single bond; and
C is a monovalent group derived from a general formula (I) and binds to B at a reactive group present in $R^1$ or $R^2$:

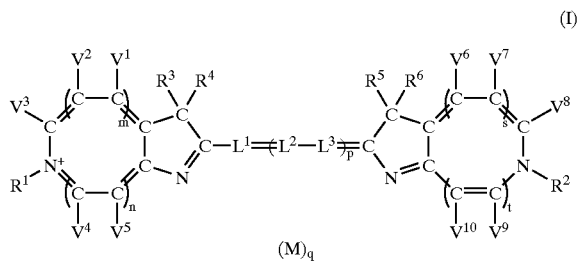

(I)

wherein $R^1$ and $R^2$ each independently represent an alkyl group that may be substituted with a reactive group capable of covalently bonding to A-B-; $R^3$, $R^4$, $R^5$, and $R^6$ each independently represent an alkyl group, and $R^3$ and $R^4$, and/or $R^5$ and $R^6$ may bind to each other to form a saturated carbon-ring together with a carbon atom(s) to which they bind; $V^1$, $V^2$, $V^3$, $V^4$, $V^5$, $V^6$, $V^7$, $V^8$, $V^9$ and $V^{10}$ each independently represent a hydrogen atom or a monovalent substituent, and two adjacent groups thereof may bind to form a ring; $L^1$, $L^2$, and $L^3$ represent a substituted or unsubstituted methine group; each of m, n, s, and t represents 0 or 1, provided that m+n=1 and s+t=1; p represents 1, 2, or 3; M represents a counter ion; and q represents a number required to neutralize the charge of a molecule.

Preferably, at least one of $R^1$ and $R^2$ is an alkyl group substituted with an active ester group capable of covalently bonding to an amino group, a hydroxyl group or a thiol group which is present in the group represented by A-B-.

Preferably, at least one of $R^1$ and $R^2$ is an alkyl group substituted with a carboxyl group.

Preferably, A is a residue of natural or synthetic nucleotide, oligonucleotide, or polynucleotide or derivative thereof.

Preferably, A is a residue of nucleotide or derivative thereof.

Preferably, A is a residue of natural or synthetic nucleotide or derivative thereof, which are selected from the group consisting of: (1) nucleotides consisting of AMP, ADP, ATP, GMP, GDP, GTP, CMP, CDP, CTP, UMP, UDP UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, and 5-MeO-CTP; (2) deoxynucleotides and dideoxynucleotides corresponding to said nucleotides; and (3) derivatives derived from said nucleotides as described in (1) and (2).

Preferably, A is a residue of avidin or streptavidin.
Preferably, B is a linking group selected from —$CH_2$—, —CH=CH—, —C. C—, —CO—, —O—, —S—, —NH— or combinations thereof, wherein a hydrogen atom on the linking group may be further substituted with a substituent.

Preferably, B is an aminoallyl group.

According to another aspect of the present invention, there is provided a process of preparing fluorescence-labeled nucleic acids which comprises the step of conducting a reaction of the synthesis of nucleic acid by using nucleic acid synthetase, a nucleic acid as a template, and the fluorescent substance of the invention.

Preferably, the reaction of the synthesis of nucleic acid is a reaction selected from the group consisting of a reverse transcription reaction, a terminal transferase reaction, a random prime method, a PCR method, and a nick-translation method.

According to further another aspect of the present invention, there is provided a nucleic acid probe or primer which is labeled with the fluorescent substance according to the invention.

According to still further another aspect of the present invention, there is provided a diagnostic agent or a reagent for detecting nucleic acids, which comprises the fluorescent substance according to the invention.

According to still further another aspect of the present invention, there is provided a kit for detecting nucleic acids, which comprises (1) the fluorescent substance according to the invention, (2) a nucleic acid synthetase, and (3) a buffer.

According to still further another aspect of the present invention, there is provided an analytical reagent or a diagnostic agent consisting of the fluorescent substance according to the invention.

According to still further another aspect of the present invention, there is provided an analytical kit, which comprises (1) the fluorescent substance according to the invention, and (2) biotin or a biotin-labeled substance.

DETAILED DESCRIPTION OF THE INVENTION

Figure 1:
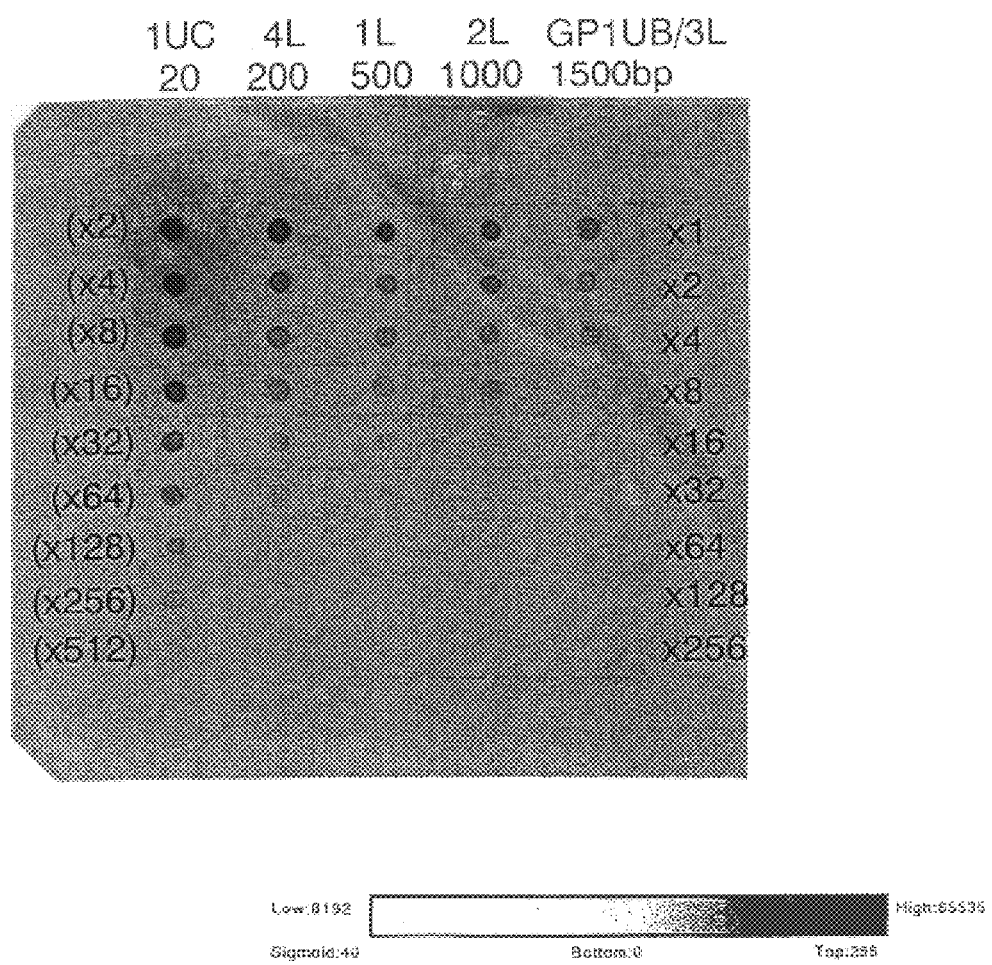
FIG. 1 shows the results of detection of biotinylated DNA using fluorescent streptavidin of the present invention.

Embodiments and practices of the present invention will now be described in more detail.

1. Fluorescent Substance of the Invention

The present invention relates to a fluorescent substance represented by a formula: A-B-C.

In the above formula, A represents a residue of natural or synthetic nucleotide, oligonucleotide, polynucleotide or derivative thereof; or A represents a residue of avidin or streptavidin.

The natural or synthetic nucleotides include, but are not limited to, a residue of natural or synthetic nucleotide, or derivative thereof, which are selected from the group consisting of: (1) nucleotides consisting of AMP, ADP, ATP, GMP, GDP, GTP, CMP, CDP, CTP, UMP, UDP UTP, TMP, TDP, TTP, 2-Me-AMP, 2-Me-ADP, 2-Me-ATP, 1-Me-GMP, 1-Me-GDP, 1-Me-GTP, 5-Me-CMP, 5-Me-CDP, 5-Me-CTP, 5-MeO-CMP, 5-MeO-CDP, and 5-MeO-CTP, (2) deoxynucleotides and dideoxynucleotides corresponding to the aforementioned nucleotides; and (3) derivatives derived from the nucleotides as described in (1) and (2). Examples of the natural or synthetic nucleotide include, but are not limited to, ATP, CTP, GTP, TTP, UTP, dATP, dCTP, dGTP, dTTP, dUTP, ddATP, ddCTP, ddGTP, ddTTP, ddUTP, or the derivatives thereof.

The oligonucleotide is obtained by polymerization of about 1 to 50, preferably 1 to 30, more preferably 1 to 20 nucleotides or derivatives thereof as described above. Each nucleotide of the constitutive unit may be identical or different. The polynucleotide is a polymer obtained by polymerization of a lot of nucleotides or derivatives thereof as described above, and its size (or length) may be, but is not specifically limited to, several base pairs (bp) to several kbp as the number of bases.

Where A represents a residue of natural or synthetic nucleotide, oligonucleotide, polynucleotide, or derivative thereof, A binds to B at a base moiety in the nucleotide residue. Examples of the base moiety of the nucleotide residue include purine derivatives and pyrimidine derivatives. In a purine base, the binding site for the linking group B is not specifically limited as long as it is other than 9-position for binding to a sugar component. For example, where the purine base is adenine, the binding site for the linking group B can be 2- or 8-position, or an amino group present at position 6; where the purine base is guanine, the binding site can be position 1 or 8, or an amino group present at position 2. In a pyrimidine base, a binding site for the linking group B is not specifically limited as long as it is other than 1-position for binding to a sugar component. For example, where the pyrimidine base is cytosine, the binding site can be 5- or 6-position, or an amino group present at 4-position; where the pyrimidine base is thymine, the binding site can be 3- or 6-position, or a methyl group present at position 5; and where the pyrimidine base is uracil, the binding site for the linking group B can be 3-, 5- or 6-position.

A may represent a residue of avidin or streptavidin. Avidin or streptavidine is a protein molecule having a molecular weight of about 60 kDa. When A represents a residue of avidin or streptavidine, the position at which A binds to a group represented by —B—C is not limited, and A can bind to —B—C at a free amino or carboxyl group on the end of the protein molecule, or at an amino group, a carboxyl group, or a hydroxyl group present on the constitutive amino acids of the protein. A linking group containing an appropriate reactive group may be previously introduced in avidin or streptavidin and the linking group may be bound to the compounds represented by general formula (I) as described below.

In the above formula, B represents a linking group or a single bond. When A represents a residue of avidin or streptavidin, B is preferably a single bond.

Types of the linking group are not specifically limited so far as they do not largely affect the characteristics of the fluorescent substance of the present invention (for example, stability of the fluorescent substance as a compound, water-solubility, uptake ratio by nucleic acid, fluorescence intensity and the like). A person skilled in the art can appropriately select a divalent linking group suitable for linking a nucleotide or avidin moiety represented by A with a fluorescent compound component represented by C.

In general, the linking group B is a linking group selected from —CH$_2$—, —CH=CH—, —C. C—, —CO—, —O—, —S—, —NH— or combinations thereof, in which a hydrogen atom on the linking group may further be substituted with any substituent. The number of carbons contained in the backbone of the linking group is not specifically limited. Generally the number of carbons ranges from 1 to 50, preferably 1 to 20, more preferably 1 to 10, most preferably 1 to 5.

In the above formula, C is a monovalent group derived from the formula (I) below, and binds to B at a reactive group present in $R^1$ or $R^2$.

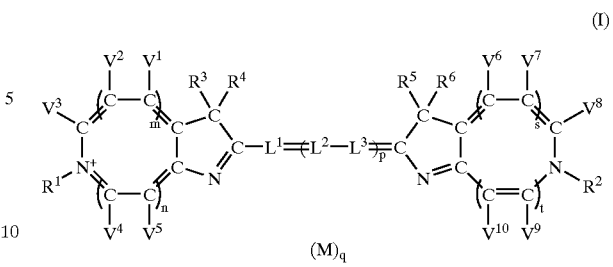

wherein $R^1$ and $R^2$ each independently represent an alkyl group which may be substituted with a reactive group capable of covalently bonding to A-B-; $R^3$, $R^4$, $R^5$, and $R^6$ each independently represent an alkyl group, or $R^3$ and $R^4$, and/or $R^5$ and $R^6$ may bind to each other to form a saturated carbon-ring together with a carbon atom(s) to which they bind; $V^1$, $V^2$, $V^3$, $V^4$, $V^5$, $V^6$, $V^7$, $V^8$, $V^9$ and $V^{10}$ each independently represent a hydrogen atom or a monovalent substituent, and two adjacent groups thereof may bind to form a ring; $L^1$, $L^2$, and $L^3$ represent a substituted or unsubstituted methine group; each of m, n, s, and t represents 0 or 1, provided that m+n=1 and s+t=1; p represents 1, 2, or 3; M represents a counter ion; and q represents a number required to neutralize the charge of a molecule.

As used herein, an alkyl moiety of an alkyl group or a substitutent containing an alkyl moiety such as an alkoxyl group, may be straight chain, branched chain, ring chain or a combination thereof, and contain about 1 to 20 carbon atoms unless otherwise specified. Alkyl groups represented by $R^1$ and $R^2$ may be identical or different. Examples of such alkyl groups include a methyl group, an ethyl group, a propyl group, an isopropyl group, a cyclopropyl group, a n-butyl group, a sec-butyl group, a tert-butyl group, a cyclopropylmethyl group, a n-pentyl group, a n-hexyl group, and a cyclohexyl group. Alkyl groups represented by $R^1$ and $R^2$ may have one or more substituents at any position on the alkyl chains. When the alkyl group contains two or more substituents, the substituents may be identical or different.

The types of the substituents on the alkyl groups represented by $R^1$ and $R^2$ are not specifically limited. It is preferred that a reactive substituent capable of forming covalent bond, ion bond, hydrogen bond and the like with a substance to be labeled, is incorporated in order to introduce a compound of the general formula (I) as a fluorescent label into a substance to be labeled including a nucleotide, avidin or streptavidin. The term "reactive substituent" as used herein means a substituent having the above characteristics.

Examples of reactive substituents which can be incorporated into each of the alkyl groups represented by $R^1$ and $R^2$ include a succinimidyl ester group, a halogen-substituted toriazinyl group, a halogen-substituted pyrimidinyl group, a sulfonyl halide group, an .-haloacetyl group, a maleimidyl group, and an aziridinyl group. In addition to these reactive substituents, examples of the reactive substituents further include a halogen atom (the term "halogen atom" used herein may be any of a fluorine atom, a chlorine atom, a bromine atom, and an iodine atom), mercapto group, cyano group, nitro group, a carboxyl group, a phosphoric acid group, a sulfo group, a hydroxyl group, an amino group, an isothiocyanate group, an isocyanate group, an alkoxyl group having carbon numbers of 1 to 8 (e.g., a methoxy group and an ethoxy group), an aryloxy group having carbon numbers of 6 to 20 (e.g., a phenoxy group, and a naphthoxy group), an alkoxycarbonyl group having carbon numbers of 2 to 10 (e.g., a methoxycarbonyl group, and an ethoxycarbonyl group), an aryloxycarbonyl group having carbon numbers of 6 to 20 (e.g., a phenoxycarbonyl group), an acyl group having carbon numbers of 2 to 10 (e.g., an acetyl group and a pivaloyl group), an acyloxy group having carbon numbers of 2 to 8 (e.g., an acetyloxy group and a benzoyloxy group), an acylamino group having carbon numbers of 2 to 8 (e.g., an acetylamino group), a sulfonyl group having carbon numbers of 1 to 8 (e.g., a methanesulfonyl group, an ethanesulfonyl group, and a benzenesulfonyl group), a sulfinyl group having carbon numbers of 1 to 20 (e.g., a methanesulfinyl group, an ethanesulfinyl group, and a benzenesulfinyl group), a sulfonylamino group having carbon numbers of 1 to 8 (e.g., a methanesulfonylamino group, an ethansulfonylamino group, and a benzenesulfonylamino group), a carbamoyl group having carbon numbers of 1 to 10 (e.g., a carbamoyl group, a methylcarbamoyl group, and a morpholinocarbamoyl group), a substituted amino group having carbon numbers of 1 to 20 (e.g., a methylamino group, a dimethyl amino group, a benzyl amino group, an anilino group, and a diphenylamino group), a sulfamoyl group having carbon numbers of 2 to 10 (e.g., a methylsulfamoyl group, an ethylsulfamoyl group, and a piperidinosulfamoyl group), an ammonium group having carbon numbers of 0 to 15 (e.g., a trimethylammonium group, and a triethylammonium group), a hydrazino group having carbon numbers of 0 to 15 (e.g., a trimethylhydrazino group), an ureido group having carbon numbers of 1 to 15 (e.g., an ureido group, and a N,N-dimehylureido group), an imide group having carbon numbers of 1 to 15 (e.g., a succinimide group), an alkylthio group having carbon numbers of 1 to 20 (e.g., a methylthio group, and an ethylthio group), an arylthio group having the carbon numbers of 6 to 20 (e.g., a phenylthio group, a p-methylphenylthio group, a p-chlorophenylthio group, a 2-pyridylthio group, and a naphthylthio group), a substituted or unsubstituted heterocyclic group having the carbon numbers of 1 to 20 (e.g., a pyridyl group, a 5-methylpyridyl group, a thienyl group, a furyl groups, a morpholino group, a tetrahydrofuryl groups, and a 2-pyradyl group), an unsaturated carbohydrate group having carbon numbers of 2 to 18 (e.g., a vinyl group, an ethynyl group, a 1-cyclohexenyl group, a benzylydine group, and a benzylidene group), a saturated or unsaturated aryl group having carbon numbers of 6 to 20 (e.g., a phenyl group, a 4-sulfophenyl group, a 2,5-disulfophenyl group, a 4-carboxyphenyl group, and a naphthyl group), and an alkyl group having carbon numbers of 1 to 20 (e.g., a methyl group, an ethyl group, and a propyl group).

Preferred examples of $R^1$ and $R^2$ include an alkyl group having carbon numbers of 1 to 15 which is substituted with a carboxyl group, an isothiocyanate group, a succinimidyl ester group, a sulfonyl halide group, an . -haloacetyl group, or a maleimidyl group; and an arylalkyl group having carbon numbers of 7 to 20 which is substituted with a carboxyl group, an isothiocyanate group, a succinimidyl ester group, a sulfonyl halide group, an . -haloacetyl group, or a maleimidyl group. More preferred examples of $R^1$ and $R^2$ include an alkyl group having carbon numbers of 1 to 10 which is substituted with a carboxyl group, an isothiocyanate group, or a succinimidyl ester group.

Examples of $R^3$, $R^4$, $R^5$ and $R^6$ include an alkyl group having carbon numbers of 1 to 20, and the alkyl group may contain any substituents illustrated in the examples of $R^1$ and $R^2$ (preferably, reactive substituents are excluded) at any position. Moreover $R^3$ and $R^4$ may bind to each other to form a saturated carbon-ring, and $R^5$ and $R^6$ may bind to each other to form a saturated carbon ring. Such saturated carbon-rings are 3- to 8-membered rings, preferably, 5- or 6-membered rings. On the carbon ring, one or more substituents such as alkyl groups may be present. Examples of $R^3$, $R^4$, $R^5$ and $R^6$ include preferably alkyl groups having carbon numbers of 1 to 6, more preferably, 1 to 3.

$V^1$, $V^2$, $V^3$, $V^4$, $V^5$, $V^6$, $V^7$, $V^8$, $V^9$ and $V^{10}$ each independently represent a hydrogen atom or a monovalent substituent. Types of substituents represented by $V^1$, $V^2$, $V^3$, $V^4$, $V^5$, $V^6$, $V^7$, $V^8$, $V^9$ and $V^{10}$ are not specifically limited and may be identical or different. Examples of these substituents include those illustrated as the substituentes on the alkyl groups represented by $R^1$ and $R^2$ (including reactive substituents).

Two groups of $V^1$, $V^2$, $V^3$, $V^4$, $V^5$, $V^6$, $V^7$, $V^8$, $V^9$ and $V^{10}$, which are adjacent to each other, may be taken together to form a saturated or unsaturated ring. Examples of the formed rings include 5- to 7-membered rings. Condensed aromatic ring may be formed as an unsaturated ring. The unsaturated ring may contain a hetero atom(s), such as oxygen atom, nitrogen atom, and sulfur atom. At any position on the formed ring, one or more of the substituents illustrated as those on the alkyl groups represented by $R^1$ and $R^2$, or an alkyl group may be substituted.

Preferred examples of $V^1$, $V^2$, $V^3$, $V^4$, $V^5$, $V^6$, $V^7$, $V^8$, $V^9$ and $V^{10}$ include a hydrogen atom, an alkyl group having carbon numbers of 1 to 6 (in which the substituents including reactive substituents, as illustrated as those on the alkyl groups represented by $R^1$ and $R^2$, may be substituted at any position), an aryl group having carbon numbers of 6 to 20 (in which the substituents including reactive substituents, as illustrated as those on the alkyl groups represented by $R^1$ and $R^2$, may be present at any position), a halogen atom, a thioalkyl group having carbon numbers of 1 to 10, an alkylsulfon group having carbon numbers of 1 to 10, a phosphoric acid group, a carboxyl group, a sulfo group, an alkoxy group having carbon numbers of 1 to 10, a substituted amino group, an isothiocyanate group, an isocyanate group, a succinimidyl ester group, a halogen-substituted triazinyl group, a halogen-substituted pyrimidinyl group, a sulfonyl halide group, an . -haloacetyl group, a maleimidyl group, and an aziridinyl group.

More preferred are hydrogen atom, a halogen atom, an aryl group having carbon numbers of 6 to 20 (which may be substituted with an isothiocyanate group, an isocyanate group, a succinimidyl ester group, a carboxyl group or a sulfo group), a sulfo group, a alkoxy group having carbon numbers of 1 to 10 (which may be substituted with an isothiocyanate group, an isocyanate group, a succinimidyl ester group, a carboxyl group or a sulfo group), an alkylthio group having carbon numbers of 1 to 10 (which may be substituted with an isothiocyanate group, an isocyanate group, a succinimidyl ester group, a carboxyl group or a sulfo group), an isothiocyanate group, a succinimidyl ester group, a sulfonyl halide group, an . -haloacetyl group, and a maleimidyl group.

$L^1$, $L^2$, and $L^3$ each independently represent a substituted or unsubstituted methine group. The number, position, and type of the substituent on the methine group are not specifically limited, and two or more substituents where present, may be identical or different. Examples of the substituents include a substituted or unsubstituted alkyl group having carbon numbers of 1 to 15, preferably 1 to 10, and more preferably 1 to 5 (e.g., a methyl group, an ethyl group, and a carboxyethyl group), a substituted or unsubstituted aryl group having carbon numbers of 6 to 30, preferably 6 to 20, more preferably 6 to 15 (e.g., a phenyl group, and an o-carboxyphenyl group), a substituted or unsubstituted hetero-cyclic ring group having carbon numbers of 3 to 20, preferably 4 to 15, more preferably 6 to 10 (e.g., a N, N-dimethyl barbiturate group), a halogen atom, an alkoxy group with carbon numbers of 1 to 20, preferably 1 to 15, more preferably 1 to 10 (e.g., a methoxy group, and an ethoxy group), an amino group having carbon numbers of 0 to 20, preferably 2 to 15, more preferably 4 to 15 (e.g., a methyl amino group, a dimethyl amino group, a N-methyl-N-phenylamino group, and a N-methyl piperazino group), an alkylthio group having carbon numbers of 1 to 15, preferably 1 to 10, more preferably 1 to 8 (e.g., a methylthio group, and an ethylthio group), and an arylthio group having carbon numbers of 6 to 20, preferably 6 to 18, more preferably 6 to 15 (e.g., a phenylthio group, and a p-methylthio group). Two of these substituents to be present on $L^1$, $L^2$, and $L^3$ may combine together to form a ring. For example, two of these substituents which are present on $L^1$, $L^2$, and $L^3$ may combine together to be an alkylene chain having carbon numbers of 2 or 3 and form a ring.

p represents 1, 2, or 3, and preferably 1 or 2. The case when p is 1 is most preferred because in this case excitation efficiency upon excitation with a semiconductor laser or helium neon laser (excitation wavelength: 630 to 650 nm) becomes very high. Each of m, n, s, or t represents 0 or 1 and satisfies the conditions of m+n=1 and s+t=1.

M represents a counter ion and may be a positive or negative ion. The positive ions may be either an inorganic positive ion or organic positive ion, and may be, for example, alkali metal ions including a sodium ion, potassium ion and lithium ion, and organic ions including a tetralkylammonium ion, and pyridinium ion. The negative ion may be either inorganic negative or organic negative ion, and may be a halogenide negative ion (e.g., fluoride ion, chloride ion, bromide ion, and iodide ion), a substituted arylsulfonate ion (e.g., p-toluenesulfonate ion, and p-chlorobenzenesulfonate ion), an aryldisulfonate ion (e.g., 1,3-benzenedisulfonate ion, and 1,5-naphthalenedisulfonate ion), an alkylsulfate ion (e.g., methylsulfate ion), a sulfate ion, a thiocyanate ion, a perchlorate ion, a tetrafluoroborate ion, a picrate ion, an acetate ion, and a trifluoromethanesulfonate ion. M may be a hydrogen ion. Preferred examples of counter-ions include an ammonium ion, an alkali metal ion, a halogenide negative ion, a substituted arylsulfonate ion, more preferably an alkali metal ion, a halogenide negative ion, and a substituted arylsulfonate ion. q represents a number required to neutralize the charge of a molecule. When a compound represented by the general formula (I) forms a intramolecular counter ion, q may be 0.

The compounds of the general formula (I) may have one or more asymmetric carbons depending on the types of substituents. The scope of the invention encompasses any stereoisomer including an optical isomer and a diastereoisomer, mixtures of stereoisomers, and racemate.

Preferable examples of the compound represented by the general formula (I) above are shown below, but the scope of the present invention is not limited by the following specific compounds.

| No. | V | R | M |
|---|---|---|---|
| I-1 | H | $-(CH_2)_5-COO^-$ | $Na^+$ |
| I-2 | H | $-CH_2-COO^-$ | $K^+$ |
| I-3 | H | $-(CH_2)_3-COO^-$ | $K^+$ |
| I-4 | H | $-(CH_2)_5-COON$(succinimide) | $ClO_4^-$ |
| I-5 | H | $-(CH_2)_5-N=C=S$ | $Cl^-$ |
| I-6 | 5-Cl | $-(CH_2)_5-COO^-$ | $Na^+$ |

-continued

| | | | |
|---|---|---|---|
| I-7 | 5-Cl | —(CH$_2$)$_5$—COON(succinimidyl) | ClO$_4^-$ |
| I-8 | 5-Cl | —(CH$_2$)$_5$—C(O)CH$_2$I | ClO$_4^-$ |
| I-9 | 5-SCH$_3$ | —(CH$_2$)$_5$—COO$^-$ | K$^+$ |
| I-10 | 5-SCH$_3$ | —(CH$_2$)$_5$—COON(succinimidyl) | ClO$_4^-$ |
| I-11 | 5-S(CH$_2$)$_5$COO$^-$ | —CH$_3$ | Na$^+$ |
| I-12 | 5-S—(CH$_2$)$_5$—COON(succinimidyl) | —(CH$_2$)$_3$—SO$_3^-$ | K$^+$ |
| I-13 | 5-OCH$_3$ | —(CH$_2$)$_5$—COO$^-$ | HN$^+$(C$_2$H$_5$)$_3$ |
| I-14 | 5-O—(CH$_2$)$_5$—COO$^-$ | —CH$_3$ | Na$^+$ |
| I-15 | 5-O—(CH$_2$)$_5$—COON(succinimidyl) | —(CH$_2$)$_4$—SO$_3^-$ | K$^+$ |
| I-16 | 5-SO$_2$CH$_3$ | —(CH$_2$)$_5$—COO$^-$ | Na$^+$ |
| I-17 | 5-SO$_2$CH$_3$ | —(CH$_2$)$_3$—COON(succinimidyl) | I$^-$ |
| I-18 | 5-Ph | —(CH$_2$)$_4$—COO$^-$ | Na$^+$ |
| I-19 | 5-Ph | —(CH$_2$)$_5$—COON(succinimidyl) | I$^-$ |

-continued
| No. | (substituent) | (chain) | M |
|---|---|---|---|
| I-20 | 5-C6H4-COOH | —(CH2)3—SO3− | Na+ |
| I-21 | 5-C6H4-SO3− | —(CH2)5—NCS | Li+ |
| I-22 | 4,5-benzo | —(CH2)3—COO− | H+ |
| I-23 | 4,5-benzo | —(CH2)5—NCS | Cl− |
| I-24 | 5-NCS | —(CH2)4—SO3− | Na+ |
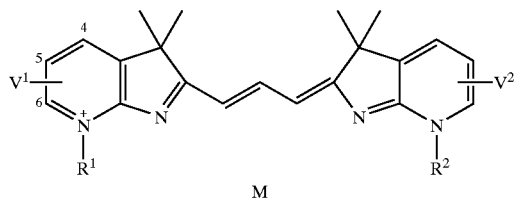
| No. | V¹ | V² | R¹ | R² | M |
|---|---|---|---|---|---|
| II-1 | H | H | CH3 | —(CH2)5—COO− | — |
| II-2 | H | H | —(CH2)4—SO3− | —(CH2)5—COO− | Na+ |
| II-3 | H | H | —(CH2)4—SO3− | —(CH2)5—COO-N-succinimidyl | — |
| II-4 | Cl | Cl | CH3 | —(CH2)5—COO-N-succinimidyl | ClO4− |
| II-5 | Cl | Cl | —(CH2)3—SO3− | —(CH2)5—NCS | — |
| II-6 | 5-S—(CH2)5—COOH | 5-SCH3 | —(CH2)4—SO3− | —(CH2)4—SO3− | Na+ |
| II-7 | 5-OCH3 | 5-OCH3 | —(CH2)3—SO3− | —CH2COO-N-succinimidyl | — |

-continued

| No. | | | | |
|---|---|---|---|---|
| II-8 | 5-O—(CH₂)₅—COON(succinimide), 5-OCH₃ | —(CH₂)₃—SO₃⁻ | —(CH₂)₃—SO₃⁻ | K⁺ |

Structure (bis-pyrrolopyridine pentamethine cyanine):

| No. | V | R | M |
|---|---|---|---|
| III-1 | H | —(CH₂)₅—COO⁻ | Na⁺ |
| III-2 | H | —(CH₂)₅—COON(succinimide) | ClO₄⁻ |
| III-3 | 5-Cl | —(CH₂)₃—NCS | ClO₄⁻ |
| III-4 | 5-Cl | —(CH₂)₅—NH—(4,6-dichloro-1,3,5-triazin-2-yl) | I⁻ |
| III-5 | 5-O—(CH₂)₅—COON(succinimide) | —(CH₂)₄—SO₃⁻ | K⁺ |
| III-6 | 5-S—(CH₂)₅—COON(succinimide) | —CH₃ | I⁻ |
| III-7 | 5-(4-COOH-C₆H₄)— | —CH₃ | ClO₄⁻ |

-continued
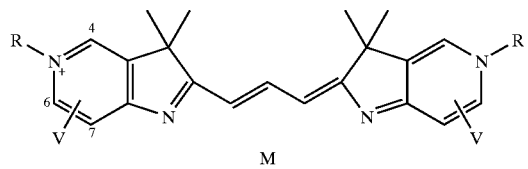
| No. | V | R | M |
|---|---|---|---|
| IV-1 | H | —(CH₂)₅—COO⁻ | Na⁺ |
| IV-2 | H | —(CH₂)₅—COON(succinimide) | ClO₄⁻ |
| IV-3 | 7-CH₃ | —(CH₂)₅—COO⁻ | K⁺ |
| IV-4 | 7-CH₃ | —(CH₂)₅—COON(succinimide) | ClO₄⁻ |
| IV-5 | 6,7-benzo | —(CH₂)₅—NCS | ClO₄⁻ |
| IV-6 | 6,7-benzo | —(CH₂)₅—C(O)CH₂I | PF₆⁻ |
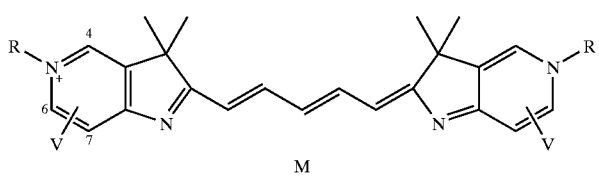
| No. | V | R | M |
|---|---|---|---|
| V-1 | H | —(CH₂)₅—COO⁻ | Na⁺ |
| V-2 | H | —(CH₂)₅—COON(succinimide) | ClO₄⁻ |
| V-3 | H | —(CH₂)₅—NCS | PF₆⁻ |

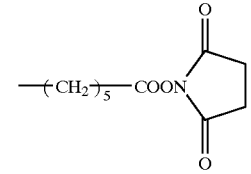

-continued

| | | | |
|---|---|---|---|
| VII-3 | 5-Cl | —(CH₂)₅—COO⁻ | K⁺ |

$$\text{M}$$

| No. | V₁ | V₂ |
|---|---|---|
| X-1 | Ph | Ph |
| X-2 | Ph | Ph |
| X-3 | 3-methoxyphenyl | 3-methoxyphenyl |
| X-4 | 3-methoxyphenyl | 3-methoxyphenyl |
| X-5 | 4-methoxyphenyl | 4-methoxyphenyl |
| X-6 | 4-methoxyphenyl | 4-methoxyphenyl |
| X-7 | 4-methoxy-3-sulfonatophenyl | 4-methoxy-3-sulfonatophenyl |
| X-8 | 4-methoxy-3-sulfonatophenyl | 4-methoxy-3-sulfonatophenyl |
| X-9 | benzofuran-2-yl | benzofuran-2-yl |
| X-10 | benzofuran-2-yl | 3-methoxyphenyl |
| X-11 | benzofuran-2-yl | 4-methoxy-3-sulfonatophenyl |

-continued
| No. | | | |
|---|---|---|---|
| X-12 | 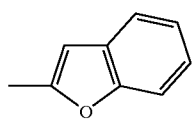 | 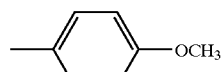 | |
| X-13 | 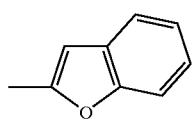 | 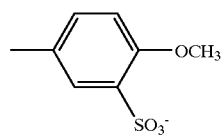 | |
| X-14 | 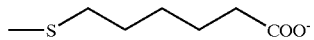 | 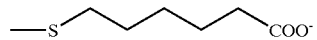 | |
| X-15 |  —Cl |  —Cl | |
| X-16 | 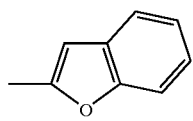 |  —Cl | |
| X-17 |  H |  H | |
| X-18 | 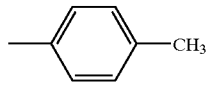 | 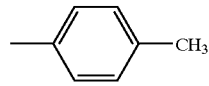 | |
| X-19 | 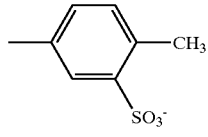 | 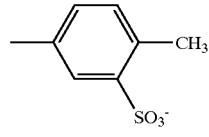 | |
| X-20 | 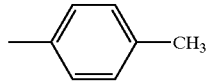 | 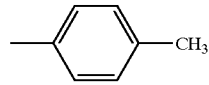 | |
| X-21 | 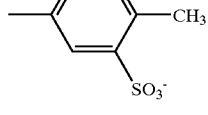 | 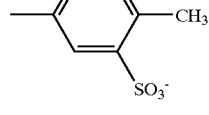 | |
| X-22 | 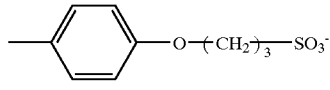 | 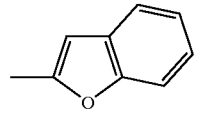 | |
| X-23 | 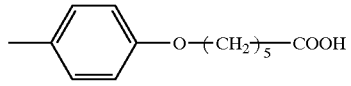 | 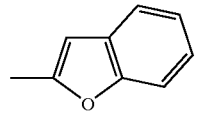 | |
| No. | $R_1$ | $R_2$ | M |
|---|---|---|---|
| X-1 | —(CH$_2$)$_5$—COO$^-$ | —(CH$_2$)$_5$—COO$^-$ | Na$^+$ |
| X-2 | CH$_3$ | —(CH$_2$)$_5$—COO$^-$ | — |
| X-3 | C$_2$H$_5$ | —(CH$_2$)$_5$—COO$^-$ | — |
| X-4 | —(CH$_2$)$_5$—COO$^-$ | —(CH$_2$)$_5$—COO$^-$ | Na$^+$ |

-continued

| ID | | | |
|---|---|---|---|
| X-5 | $-(CH_2)_4-SO_3^-$ | $-(CH_2)_5-COO-N(succinimide)$ | — |
| X-6 | $CH_3$ | $-(CH_2)_5-COO^-$ | — |
| X-7 | $CH_3$ | $-(CH_2)_5-COOH$ | $K^+$ |
| X-8 | $C_2H_5$ | $-(CH_2)_5-COO-N(succinimide)$ | $Na^+$ |
| X-9 | $-(CH_2)_5-COO^-$ | $-(CH_2)_5-COO^-$ | $Na^+$ |
| X-10 | $-(CH_2)_4-SO_3^-$ | $-(CH_2)_5-COOH$ | — |
| X-11 | $-(CH_2)_4-SO_3^-$ | $-(CH_2)_5-COOH$ | $K^+$ |
| X-12 | $-(CH_2)_4-SO_3^-$ | $-(CH_2)_5-COOH$ | — |
| X-13 | $-(CH_2)_4-SO_3^-$ | $-(CH_2)_5-COOH$ | $K^+$ |
| X-14 | $CH_3$ | $CH_3$ | $Na^+$ |
| X-15 | $-(CH_2)_5-COO^-$ | $-(CH_2)_5-COO^-$ | $Na^+$ |
| X-16 | $-(CH_2)_4-SO_3^-$ | $-(CH_2)_5-COOH$ | — |
| X-17 | $-(CH_2)_5-COOH$ | $-(CH_2)_5-COOH$ | $Na^+$ |
| X-18 | $-(CH_2)_5-COO^-$ | $-(CH_2)_5-COO^-$ | $Na^+$ |
| X-19 | $-(CH_2)_5-COO^-$ | $-(CH_2)_5-COO^-$ | $3Na^+$ |
| X-20 | $-CH_3$ | $-(CH_2)_5-COO^-$ | $Na^+$ |
| X-21 | $-CH_3$ | $-(CH_2)_5-COOH$ | $Na^+$ |
| X-22 | $-(CH_2)_5-COOH$ | $-(CH_2)_4-SO_3^-$ | $Na^+$ |
| X-23 | $-(CH_2)_4-SO_3^-$ | $-(CH_2)_4-SO_3^-$ | $Na^+$ |

Examples of the process of preparing the typical compounds are described in the Examples of the present specification. Referring to the practical explanation given in the Examples, a person skilled in the art can prepare any compounds represented by the general formula (I) above by appropriately selecting a starting compound, reaction conditions, reagents and the like, and modifying and altering the methods shown in the examples if necessary. It is easily understood that the process of preparing the compounds represented by the general formula (I) above is not specifically limited and compounds prepared by any process can be used in the present invention. The compound represented by the general formula (I) is also described in Japanese Patent Application No. 11-264845, which is incorporated herein by reference in its entirety.

The compound represented by the general formula (I) is used as a fluorescent labeling component in the fluorescent substance of the present invention.

Various techniques for introducing the compound represented by the general formula (I) as a fluorescent label into a nucleotide and avidin or streptavidin are known, and techniques which are available for a skilled person in the art can be suitably selected and used. For example, a functional group such as an amino group or a hydroxyl group in nucleotide, or an amino group, a carboxyl group or a hydroxyl group in avidin or streptavidin may be directly bound to a reactive substituent such as a carboxyl group or an active ester group in the compound of the general formula (I) via ion bond or covalent bond; or after chemical modification such as incorporation of a linking group (or linker) into a part of the nucleotide, avidin or streptavidin, the compound of the general formula (I) may be allowed to be reacted.

The fluorescent substance obtained after reaction can be purified by general separation techniques, such as chromatography, electrophoresis and re-crystallization.

2. Use of the Fluorescent Substance of the Invention

The present invention further relates to the use of the fluorescent substance of the present invention. The fluorescent substance of the present invention can be used as fluorescent nucleotides (hereinafter referred to as "fluorescent nucleotide") when A represents a residue of natural or a synthetic nucleotide, oligonucleotide, or polynucleotide or derivative thereof in the formula: A-B-C; and it can be used as fluorescent avidin (hereinafter referred to as fluorescent avidin of the present invention) when A represents the residue of avidin or streptavidin. The term "fluorescent nucleotide" in this specification encompasses all cases when A in the formula A-B-C represents a residue of natural or synthetic nucleotide, oligonucleotide, or polynucleotide, or derivative thereof, and the term "fluorescent avidin" in this specification encompasses both cases when A in the formula A-B-C represents the residue of avidin or streptavidin. The use of the fluorescent nucleotide of the present invention and the fluorescent avidin of the present invention will be described below.

(A) Use of Fluorescent Nucleotide of the Invention

The fluorescent nucleotide of the present invention can be used for detecting nucleic acids.

When the fluorescent nucleotide of the present invention is used for DNA analysis such as detection of nucleic acids, the fluorescent nucleotide of the present invention can be incorporated into a probe or a primer by Ruth's technique (Jerry L. Ruth, DNA, 3, 123, 1984). The present invention further provides a process of preparing fluorescence-labeled nucleic acids which comprises the step of conducting a reaction of the synthesis of nucleic acid by using nucleic acid synthetase, a nucleic acid as a template, and the fluorescent nucleotide of the present invention.

Examples of nucleic acid synthetase used herein include, but are not limited to, DNA polymerase (any DNA polymerase, such as Klenow enzyme, Taq DNA polymerase and the like), RNA polymerase, reverse transcriptase, or terminal transferase. The type of a nucleic acid as a template may be DNA or RNA, and may be natural DNA or RNA, recombinant DNA or RNA, or chemically-synthesized DNA or RNA. The reaction of the synthesis of nucleic acid may be performed under conditions (e.g., salt concentration, pH, and temperature) suitable for enzymatic reaction using template DNA, non-fluorescent nucleotide mixture, the fluorescent nucleotide of the present invention and nucleic acid synthetase. These methods of synthesizing nucleic acids are well-known to a person skilled in the art. A person skilled in the art can appropriately select substances and reagents according to their purposes for labeling.

Various methods can be used to label nucleic acids (DNA or RNA) using the fluorescent nucleotide of the present invention.

The random prime method is one of the methods for labeling DNA, wherein a mixture of optionally combined hexanucleotide sequences is used as a primer (i.e., random primer), and the random primer is hybridized to a nucleic acid to be labeled. Starting from 3'-OH terminus of this random primer, a strand complementary to the single strand is synthesized using DNA polymerase such as Klenow enzyme, or other DNA polymerase. 4 types of deoxyribonucleotide, a substrate for DNA polymerase, are introduced into the complementary strand. By using the fluorescent nucleotide of the present invention as one type of these deoxyribonucleotide, complementary DNA labeled with the fluorescent nucleotide is synthesized.

Instead of a random primer, oligo DNA having a specific sequence (specific primer) can be used. The specific primer binds to a complementary region in a template DNA, then the synthesis of DNA complementary to the template DNA starts from the 3'-OH terminus of the specific primer. As in the case of the random prime method, the fluorescent nucleotide of the present invention is incorporated during the synthesis of complementary DNA, thereby fluorescence-labeled complementary DNA is synthesized.

Nick translation is a method using the action of DNase I on double-stranded DNA. The action of DNase I creates a cleavage site at which the template double-stranded DNA is cut into a single strand. Simultaneously E.coli DNA polymerase I, 4 types of deoxyribonucleotides that are substrates of this enzyme, and the fluorescent nucleotide of the present invention are added to the reaction mixture. E.coli DNA polymerase I cleaves a 5'-terminal deoxyribonucleotide of the cleaved single strand and simultaneously inserts one substrate deoxyriboucleotide at a site adjacent to the free 3'-OH terminus. By repeating this process, the cleavage site moves toward the 3' terminus. By containing the fluorescent nucleotide of the present invention in the substrate nucleotide, fluorescent DNA can be synthesized by nick translation.

To label the 3' terminus of double- or single-stranded DNA, terminal transferase, which is an enzyme to bind a deoxyribonucleotide or ribonucleotide to the 3'-OH terminus, can be used. The terminal transferase requires at least one type of deoxyribonucleotide or ribonucleotide as a substrate. By using the fluorescent nucleotide of the present invention as a substrate for the terminal transferase, fluorescence-labeled nucleic acids elongating from the 3'-OH terminus can be synthesized.

Reverse transcription is a reaction to synthesize complementary DNA from a single-stranded RNA. After annealing an oligodeoxyribonucleotide as a primer to a complementary portion of RNA, an elongation reaction is performed using reverse i transcriptase, thereby synthesizing DNA strand complementary to RNA strand starting form the 3'-OH terminus of the primer. In this DNA synthesis, four types of deoxyribonucleotides are used as substrates for enzymes. The use of the fluorescent nucleotide of the present invention as one of these substrates allows the fluorescent nucleotide to be inserted into elongating DNA strand during reverse transcription so that fluorescence-labeled DNA is synthesized.

RNA labeled with the fluorescent nucleotide of the present invention can be synthesized using an enzyme that synthesizes RNA from DNA. Such enzymes that synthesize RNA from DNA include RNA polymerase encoded by a phage, such as SP6, T3 or T7 RNA polymerase. These enzymes are those for synthesizing double-stranded DNA and RNA containing SP6, T3 or T7 promoter, and four types of ribonucleotides are used as substrates. By using the fluorescent nucleotide of the present invention as one of the substrates, fluorescence-labeled RNA can be synthesized.

Alternatively, nucleic acids labeled with the fluorescent nucleotide of the present invention can be synthesized by polymerase chain reaction (PCR). In PCR, nucleic acids to be detected in the biological sample are denatured into a single strand, and two types of primers are annealed to the single-stranded nucleic acids. After annealing, elongation reaction is conducted using polymerase (preferably Taq DNA polymerase) and deoxyribonucleotides as enzyme substrates. Complementary DNA is synthesized starting from the 3'-OH terminus of the primer, thereby forming double-stranded DNA. By repeating this process, DNA to be detected in the sample can be amplified. By using the fluorescent nucleotide of the present invention as one of the substrates during elongation reaction by Taq DNA polymerase, fluorescence-labeled nucleotides can be amplified.

Fluorescent nucleic acids labeled with the fluorescent nucleotide of the present invention prepared as described above can be used as gene probes for detecting homologous nucleic acid sequences by hybridization. Fluorescent nucleotide to which a target nucleic acid was hybridized, can easily be detected by measuring the fluorescence intensity using a fluorometer.

As described above, the fluorescent nucleotide of the present invention is useful as a diagnostic agent or as a regent for detecting nucleic acids since the fluorescent nucleotide of the present invention can be used for labeling gene probes.

When the fluorescent nucleotide of the present invention is used as a diagnostic agent or as a regent for detecting nucleic acids, it can be supplied in the form of a reagent composition in combination with one or more types of additives. For example, the reagent can be prepared in a desired form such as a solution, using a proper additive(s), including a buffer, a solubilizer, a pH modifier, and a preservative. A person skilled in the art can appropriately select the form of reagent and the process for the preparation thereof.

Furthermore, the fluorescent nucleotide of the present invention can be supplied in the form of a kit for detecting nucleic acids, together with an enzyme usable in the above described nucleic acid biosynthetic reaction, a buffer, and the like. Types of reagents to be contained in the kit can be appropriately selected according to the purpose of the kit. Such reagents may include a mixture of one or more (preferably 4) non-fluorescent nucleotides, purified water, or the like, in addition to the fluorescent nucleotide, nucleic acid synthetase, and buffer. The kit can further contain random primers, an oligo dT primer, or a specific primer according to purposes.

(B) Use of the Fluorescent Avidin of the Invention

The fluorescent avidin of the present invention can be used to detect biological components such as nucleic acids, proteins or sugars.

To use the fluorescent avidin of the present invention for DNA analysis such as detection of nucleic acids, for example, it is preferred that biotin is previously incorporated into a probe or primer to be detected by the fluorescent avidin of the invention. When the fluorescent avidin of the present invention is added to a probe or primer having biotin, biotin and (strept) avidin couple together to form a complex due to the affinity between them. By measuring a fluorescence of the complex, the probe or the primer can be detected.

A method for preparing a biotin-labeled probe or a biotin-labeled primer is known to a person skilled in the art. For example, biotin-labeled nucleic acids can be synthesized using a biotin-labeled nucleotide (e.g., biotinylated dUTP) by a method including a random prime method, a nick translation method and a terminal transferase method, or by reverse transcription, polymerase chain reaction (PCR) or the like. The biotin-labeled nucleic acid so obtained can be used as a probe or primer to be detected by the fluorescent avidin of the invention.

Similarly, the fluorescent avidin of the present invention can be used to analyze proteins. For example, biotin-labeled antibody is reacted with a biological sample, then with the fluorescent avidin of the present invention, thereby forming a complex between the labeled antibody and the fluorescent avidin of the invention. The presence of the biotin-labeled antibody, that is indicative of the presence of a target protein in the biological sample, can be detected by measuring the fluorescence of this complex.

For example, the presence of cancer cell or cancer tissue can be proved by labeling an anti-tumor antibody with biotin, contacting the labeled antibody with tissues or organs, then allowing the product to be reacted with the fluorescent avidin of the present invention. For diagnosis, for example a tissue section may be observed under a microscope by fixing it by a proper method such as paraffin method; or the tissue section may be observed with an endoscope after immunochemically staining the biological tissue. Recently, various fluorescent imaging methods using near infrared ray fluorescent substances have been proposed (e.g., Japanese Patent Application Laid-Open No. 9-309845; J. Neurosurg., 87, pp. 738–745, 1997; Medical Electronics and Bioengineering, 34, pp. 316–322, 1996). The fluorescent avidin of the present invention can be used as a diagnostic agent for fluorescent imaging procedures.

Fluorescence of the fluorescent avidin of the present invention to which a biotin-component in a substance to be detected (nucleic acid, protein or sugar) is bound can be readily detected by measuring the fluorescence intensity using a fluorometer.

As described above, the fluorescent avidin of the present invention is useful as a reagent for analyzing biological components.

To use the fluorescent avidin of the present invention as an analytical reagent or a diagnostic agent, it can be supplied in the form of a reagent composition in combination with one or more types of additives. For example, the reagent can be prepared in a desired form such as a solution, by using an appropriate additive(s), including a buffer, a solubilizer, a pH modifier, and a preservative. A person skilled in the art can appropriately select the form of reagent and the process for the preparation thereof.

The fluorescent avidin of the present invention can also be supplied in the form of an analytical kit together with biotin or biotin-labeled substances. The type of a reagent to be contained in the kit can be appropriately selected according to purposes of the kit. In addition to the fluorescent avidin of the present invention, and biotin or a biotin-labeled substance (e.g., a biotin-labeled nucleotide or a biotin-labeled antibody), a primer (e.g., a random primer, an oligo dT primer, and a specific primer), nucleotide mixture, a buffer, purified water or the like can also be used in combination depending on purposes of the kit.

The present invention is further described in the following examples. These examples are provided for illustrative purposes only, and are not intended to limit the scope of the invention. Those skilled in the art will realize that various changes, modifications and substitutions of materials and methods described in examples may be made without departing from the spirit of the invention.

EXAMPLES

Each of Compounds 1, 4, 6, 7, 9, 10, 11, 12, 13, 14, 17 and 18 to 22, which were synthesized in the following synthesis examples, corresponds to compounds X-1, X-4, X-6, X-7, X-9, X-10, X-11, X-12, X-13, X-14, X-17 and X-18 to X-22 which are illustrated herein as preferred compounds.

Synthesis Example 1

Synthesis of Compound 1

The synthesis scheme of Compound 1 is shown below:

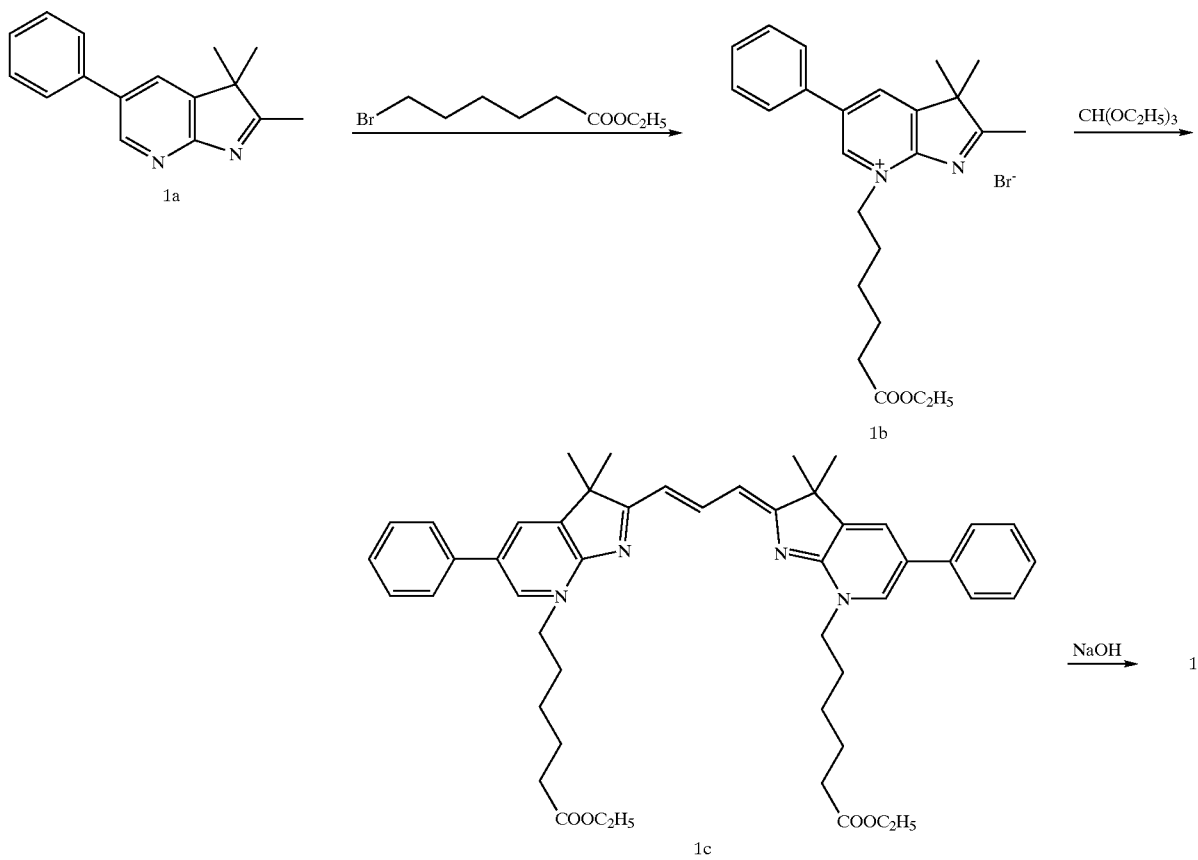

(Synthesis of Compound 1b)

Compound 1a (2.36 g, 10 mmol) was dissolved in acetone (10 ml), ethyl 6-bromohexanoate (3.3 g, 15 mmol) was added thereto, and the mixture was heated under reflux for 5 hours. In this reaction, alkylation to heterocyclic nitrogen (indole ring part) occurred other than at the target site. However, an oil component generated by adding ethyl acetate (50 ml) and hexane (50 ml) to the reaction solution was separated out by decantation, ethyl acetate (10 ml) and isopropyl alcohol (5 ml) were added to this oil, and the mixture was heated under reflux for 30 minutes, thereby allowing crystallization of only Compound 1b, which was the product of interest where pyridine ring nitrogen is quaternary.

Amount: 2.8 g, Yield: 60%

(Synthesis of Compound 1c)

Compound 1b (2.3 g, 5 mmol) was dissolved in a mixed solvent of pyridine (5 ml) and acetic acid (2 ml). Triethyl orthoformate (1 ml) and triethylamine (1 ml) were added thereto and the mixture was reacted at 140° C. for 1 hour. By adding ethyl acetate (50 ml) to the reaction solution, a solid containing Compound 1c was deposited. The solid was collected by filtration and was used for the following reaction without purification.

Mass (posi): 768

(Synthesis of Compound 1)

The total amount of the above-mentioned unpurified Compound 1c was dissolved in methanol (10 ml), tetrahydrofuran (5 ml) and water (10 ml). 10% sodium hydroxide solution (5 ml) was added thereto and then the mixture was reacted at room temperature for 30 minutes. After adding saturated sodium bicarbonate solution (10 ml) to the reaction solution, the mixture was concentrated under vacuum to deposit the crude crystal of Compound 1. The crude crystal was purified by gel filtration (SEPHADEX LH-20) to obtain Compound 1.

Amount: 0.7 g, Yield: 40% (from Compound 1b)

Mass (nega): 709 (M−Na)

Absorption maximum (methanol): 634 nm

Molecular absorption coefficient: 190,000

Synthesis Example 2

Synthesis of Compound 4

Compound 4 was synthesized in the same method as in Compound 1, with the exception that Compound 1a was substituted with 5-(3-methoxyphenyl)-7-azaindolenine.
Mass (nega): 769 (M–Na)
Absorption maximum (methanol): 636 nm Molecular absorption coefficient: 190,000

Synthesis Example 3

Synthesis of Compound 9

Compound 9 was synthesized in the same method as in Compound 1, with the exception that Compound 1a was substituted with 5-benzofuranyl-7-azaindolenine.
Mass (nega): 790 (M–Na)
Absorption maximum (methanol): 658 nm Molecular absorption coefficient: 200,000

Synthesis Example 4

Synthesis of Compound 6

The synthesis scheme of Compound 6 is shown below:

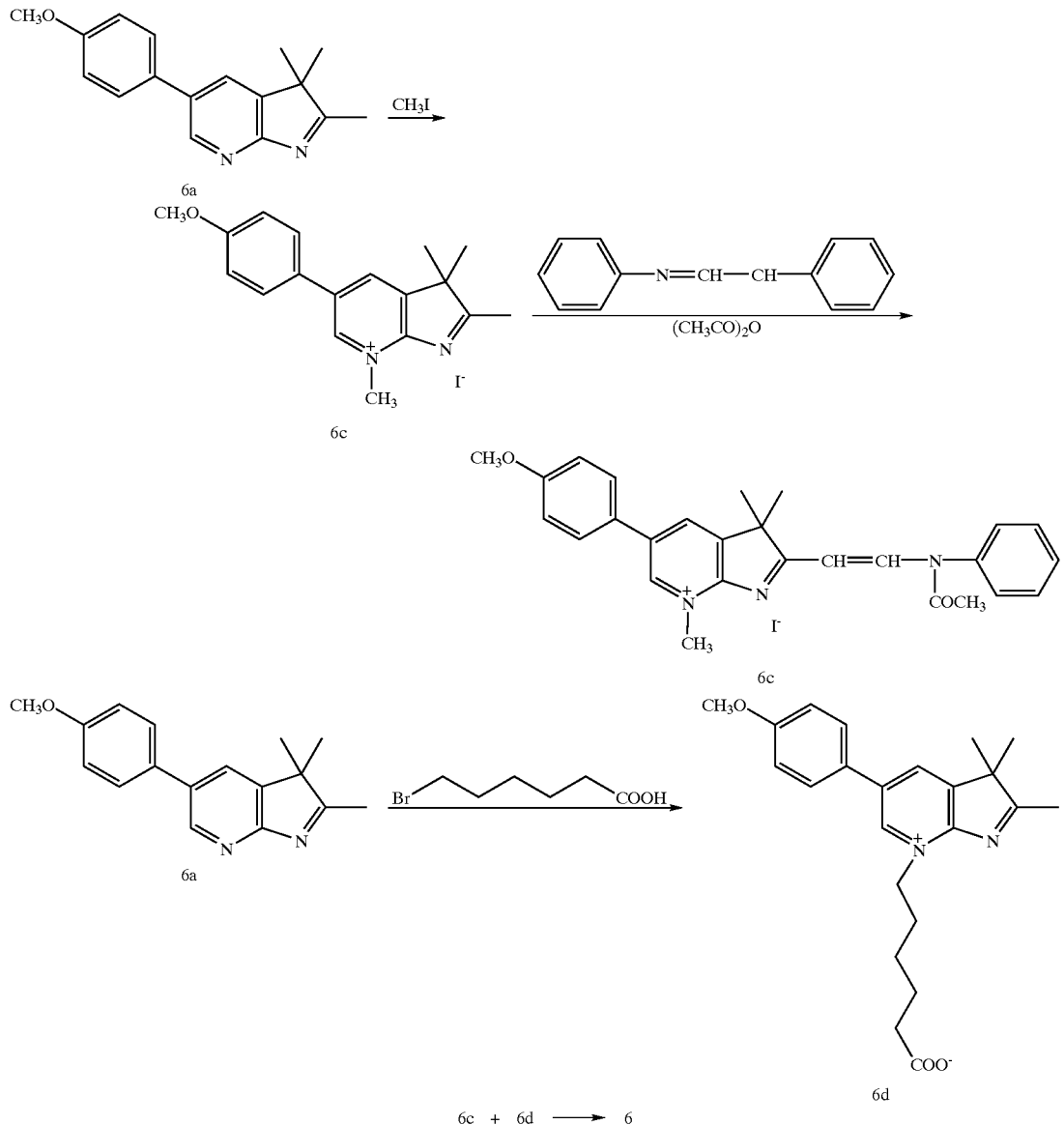

(Synthesis of Compound 6b)

Compound 6a (2.7 g, 10 mmol) was dissolved in acetone (10 ml), iodomethane (4.3 g, 30 mmol) was added thereto, and the mixture was heated under reflux for 2 hours. The pale yellow crystal of Compound 6b, which began to be deposited 1 hour after the start of the reaction, was filtrated by adding ethyl acetate (20 ml) to obtain Compound 6b.
Amount 3.2 g, Yield: 80%
Mass (posi): 281

(Synthesis of Compound 6c)

Compound 6b (4.1 g, 10 mmol), N,N'-diphenylformamidine (9.8 g, 50 mmol) and acetic anhydride (5 ml) were mixed and reacted at 60° C. for 1 hour, and then 100° C. for 3 hours.

Ethyl acetate (50 ml) was added to the reaction solution to deposit Compound 6c.
Amount: 3.3 g, Yield: 60%
Mass (posi): 426
(Synthesis of Compound 6d)

Compound 6a (2.66 g, 10 mml) was dissolved in dimethylformamide (10 ml), and ethyl 6-bromohexanoate (5.9 g, 30 mmol) was added thereto followed by reaction at 120° C. for 1.5 hours. In this reaction, alkylation to heterocyclic nitrogen (indole ring part) occurred other than at the target site. However, an oil component generated by adding ethyl acetate (50 ml) to the reaction solution, was separated out by decantation and crystallized with diethyl ether to obtain only Compound 6d, which is the product of interest where pyridine ring nitrogen is quaternary.
Amount: 2.3 g; Yield: 60%
Mass (posi): 380
(Synthesis of Compound 6)

Compound 6c (2.76 g, 5 mmol) and Compound 6d (1.9 g, 5 mmol) were dissolved in dimethylformamide (20 ml), and triethylamine (2 ml) was added thereto followed by reaction at room temperature for 30 minutes.

The crude crystal of Compound 6 was deposited by adding ethyl acetate (30 ml) to the reaction solution.

The obtained crude crystal was purified by recrystallization from methanol to obtain Compound 6.
Amount: 1.8 g, Yield: 55%
Mass (nega): 671
Absorption maximum (methanol): 637 nm
Molecular absorption coefficient: 190,000

Synthesis Example 5

Synthesis of Compound 7

Compound 6 (0.67 g, 1 mmol) was dissolved in dimethylformamide (2 ml), and a sulfur rolioxidedimethylformamide complex (0.76 g, 5 mmol) was added thereto followed by reaction at 90° C. for 5 hours. Acetone (30 ml) was added to the reaction solution to deposit the crude crystal of Compound 7, which was collected by filtration. The crude crystal was dissolved in methanol, and potassium acetate (0.5 g) was added to carry out a salt-forming reaction, whereby Compound 7 was deposited.
Amount: 0.59 g, Yield: 65%
Mass (nega): 868
Absorption maximum (methanol): 640 nm
Molecular absorption coefficient: 190,000

Synthesis Example 6

Synthesis of Compound 10

The synthesis scheme of Compound 10 is shown below:

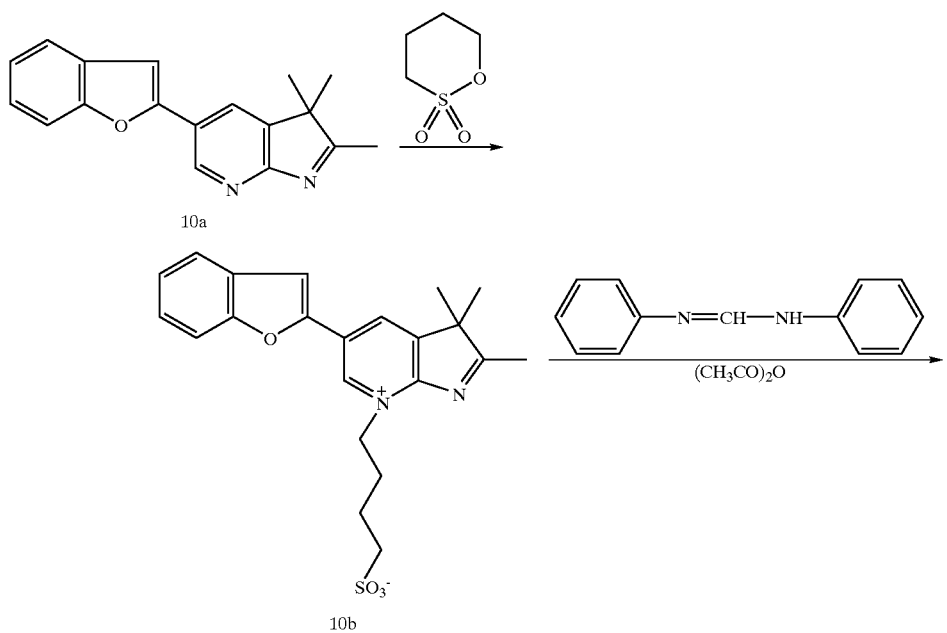

-continued

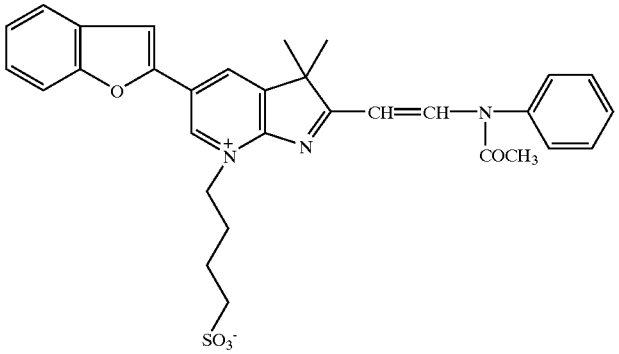

10c

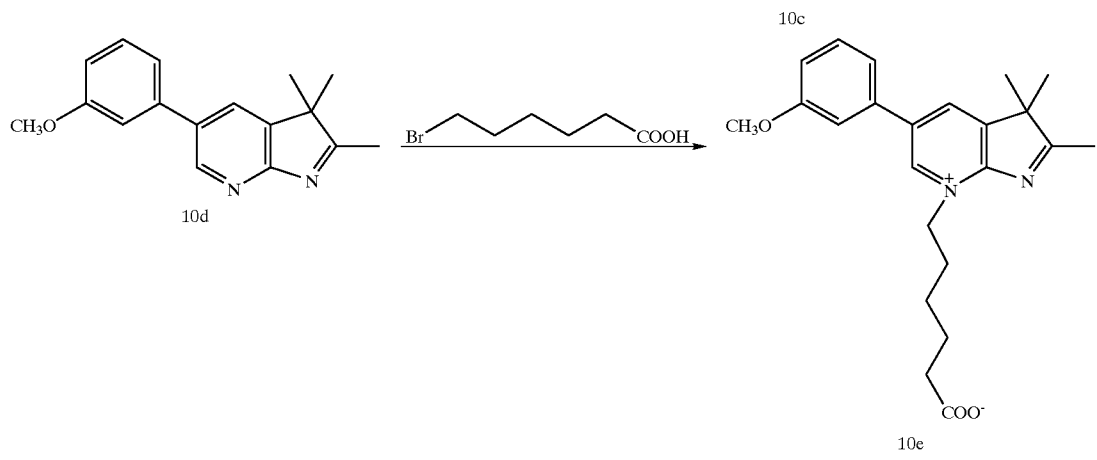

10c + 10e → 10

(Synthesis of Compound 10b)
Compound 10a (2.76 g, 10 mmol) was dissolved in acetone (10 ml), butanesultone (2.0 g, 15 mmol) was added thereto, and the mixture was heated under reflux for 5 hours deposit Compound 10b. Ethyl acetate (20 ml) was added thereto to collect the compound by filtration.
Amount: 3.3 g, Yield: 80%
Mass (posi): 412

(Synthesis of Compound 10c)
Compound 10b (4.1 g, 10 mmol), N,N'-diphenylformamidine (9.8 g, 50 mmol) and acetic anhydride (5 ml) were mixed and reacted at 60° C. for 1 hour, and then at 100° C. for 3 hours.
Ethyl acetate (50 ml) was added to the reaction solution to deposit Compound 10c.
Amount: 2.8 g, Yield: 50%
Mass (posi): 557

(Synthesis of Compound 10e)
Compound 10e was synthesized from compound 10d according to the method for the synthesis of Compound 6d.
Mass (posi): 380

(Synthesis of Compound 10)
Compound 10c (2.79 g, 5 mmol) and Compound 6d (1.9 g, 5 mmol) were dissolved in dimethylformamide (20 ml). Triethylamine (2 ml) was added thereto and the mixture was reacted at room temperature for 30 minutes.
By adding methyl acetate (30 ml) to the reaction solution, the crude crystal of compound 10 was deposited.
The crude crystal was purified by recrystallization from the mixed solvent of methanol and chloroform to obtain Compound 10.
Amount: 1.8 g, Yield: 45%

Mass (nega): 803
Absorption maximum (methanol): 646 nm
Molecular absorption coefficient: 190,000

Synthesis Example 7

Synthesis of Compound 11

Compound 10 (0.80 g, 1 mmol) was dissolved in dimethylformamide (2 ml), and a sulfur rolioxidedimethylformamide complex (0.46 g, 3 mmol) was added thereto followed by reaction at 90° C. for 5 hours. Acetone (30 ml) was added to the reaction solution to deposit crude crystal of Compound 11, which was collected by filtration. The crude crystal was dissolved in methanol, and potassium acetate (0.5 g) was added to carry out a salt-forming reaction, whereby Compound 11 was deposited.
Amount: 0.46 g, Yield: 50%
Mass (nega): 882
Absorption maximum (methanol): 648 nm
Molecular absorption coefficient: 190,000

Synthesis Example 8

Synthesis of Compound 12

Compound 12 was synthesized according to the method for the synthesis of Compound 10.
Mass (nega): 803
Absorption maximum (methanol): 646 nm
Molecular absorption coefficient: 190,000

Synthesis Example 9

Synthesis of Compound 13

Compound 13 was synthesized according to the method for the synthesis of Compound 11.

Mass (nega): 882
Absorption maximum (methanol): 648 nm
Molecular absorption coefficient: 190,000

Synthesis Example 10

Synthesis of Compound 14

The synthesis scheme of Compound 14 is shown below:

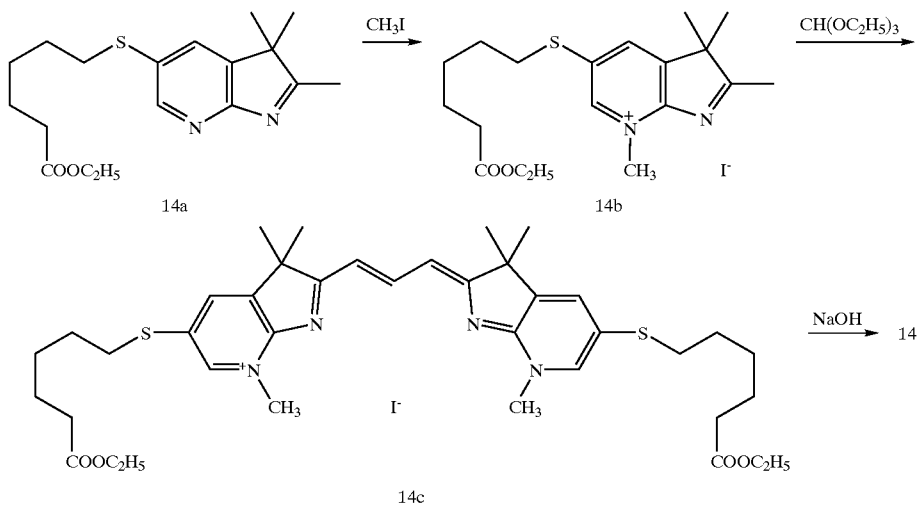

(Synthesis of Compound 14b)

Compound 14a (1.9 g, 10 mmol) was dissolved in acetone (10 ml), iodomethane was added thereto, and the mixture was heated under reflux for 2 hours. The crystal deposited by adding methyl acetate (40 ml) to the reaction solution was collected by filtration to obtain Compound 14b.

Amount: 4.0 g, Yield: 85%
Mass (posi): 349

(Synthesis of Compound 14c)

Compound 14b (2.4 g, 5 mmol) was dissolved in a mixed solvent of pyridine (5 ml) and acetic acid (2 ml). Triethyl orthoformate (1 ml) and triethylamine (1 ml) were added and the mixture was reacted at 140° C. for 1 hour. By adding ethyl acetate (50 ml) and hexane (50 ml) to the reaction solution, a solid containing Compound 14c was deposited. The solid was collected by filtration and was used for the following reaction without purification.

Mass (posi): 708

(Synthesis of Compound 14)

The total amount of the above unpurified Compound 14c was dissolved in methanol (10 ml), tetrahydrofuran (5 ml) and water (10 ml). A solution of 10% sodium hydroxide (5 ml) was added thereto and the mixture was reacted at room temperature for 2 hours. After adding saturated sodium bicarbonate solution (10 ml) to the reaction solution, the mixture was concentrated under vacuum to deposit the crude crystal of Compound 14. The crude crystal was purified by gel filtration (SEPHADEX LH-20) to obtain Compound 14.

Yield: 0.59 g, Yield rate: 35% (from Compound 14b)
Mass (nega): 650 (M–Na)
Absorption maximum (methanol): 632 nm
Molecular absorption coefficient: 170,000

Synthesis Example 11

Synthesis of Compound 17

The synthesis scheme of Compound 17 is shown below:

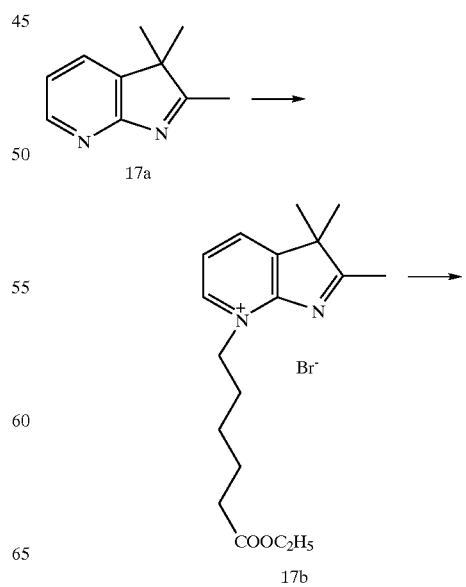

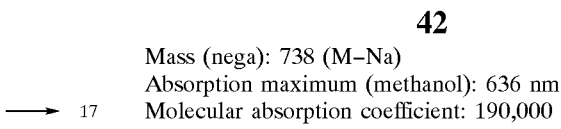

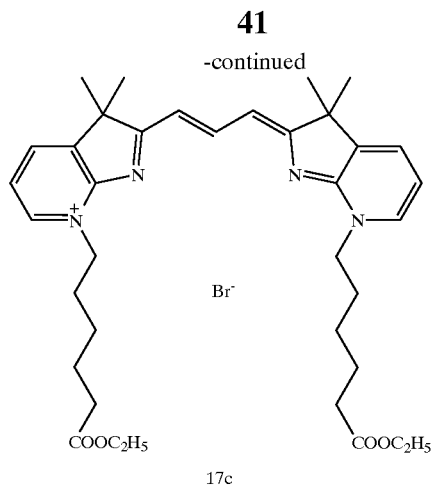

17c (Synthesis of Compound 17b)

Compound 17a (2.6 g, 16.2 mmol) was dissolved in acetone (10 ml), ethyl 6-bromohexanoate (3.6 g, 16.2 mmol) was added thereto, and the mixture was heated under reflux for 5 hours. In this reaction, alkylation to heterocyclic nitrogen (indole ring part) occurred other than at the target site. However, an oil component generated by adding ethyl acetate (50 ml) and hexane (50 ml) to the reaction solution, was separated out by decantation, and ethyl acetate (10 ml) and isopropyl alcohol (5 ml) were added to this oil and the mixture was heated under reflux for 30 minutes thereby allowing crystallization of only Compound 17b, which is the product of interest where pyridine ring nitrogen is quaternary.

Amount: 4.0 g, Yield: 65%
Mass (posi): 337

(Synthesis of Compound 17c)

Compound 17b (4.0 g, 10.4 mmol) was dissolved in a mixed solvent of pyridine (5 ml) and acetic acid (2 ml). Triethyl orthoformate (2 ml) and triethylamine (0.5 ml) were added thereto followed by reaction at 140° C. for 1 hour. By adding ethyl acetate (50 ml) and hexane (50 ml) to the reaction solution, a solid containing Compound 17c was deposited. The solid was collected by filtration and was used for the next reaction without purification.

Mass (posi): 615

(Synthesis of Compound 17)

The total amount of the above-mentioned unpurified Compound 17c was dissolved in methanol (10 ml) and water (10 ml). A solution of 10% sodium hydroxide (5 ml) was added thereto and the mixture was reacted at room temperature for 30 minutes. After adding a saturated sodium bicarbonate solution (10 ml) to the reaction solution, the crude crystal of Compound 17 was deposited by vacuum concentration. The crude crystal was purified by gel filtration (SEPHADEX LH-20) to obtain Compound 17.

Amount: 1.5 g, Yield: 50% (from Compound 17b)
H-NMR (DMSO-d6)δ; 8.90 (t, 1H), 8.08 (d, 2H), 7.80 (d, 2H), 6.98 (t, 2H), 6.00 (d, 2H), 4.42 (t, 4H), 2.13 (t, 4H), 1.78 (m, 4H), 1.58 (m, 4H), 1.37 (s, 12H), 1.12 (m, 4H)
Absorption maximum (methanol): 609 nm
Molecular absorption coefficient: 120,000

Synthesis Example 12

Synthesis of Compound 18

Compound 18 was synthesized in the same way as the method used for Compound 1, with the exception that Compound 1a was substituted with 5-(4-methylphenyl)-7-azaindolenine.

Mass (nega): 738 (M−Na)
Absorption maximum (methanol): 636 nm
Molecular absorption coefficient: 190,000

Synthesis Example 13

Synthesis of Compound 19

Compound 18 was dissolved in concentrated sulfuric acid, and the mixture was reacted at 100° C. for 30 minutes. The reaction solution was cooled on ice, and the pH was adjusted to pH 8 with 10% sodium hydroxide solution, followed by vacuum concentration. The obtained residue was purified with Sephadex LH20 three times to obtain Compound 19.

Mass (nega): 942 (M−Na)
Absorption maximum (methanol): 636 nm
Molecular absorption coefficient: 190,000

Synthesis Example 14

Synthesis of Compound 20

Compound 20 was synthesized in the same way as the method used for Compound 6, with the exception that Compound 6a was substituted with 5-(4-methylphenyl)-7-azaindolenine.

Mass (nega): 639 (M−Na)
Absorption maximum (methanol): 636 nm
Molecular absorption coefficient: 190,000

Synthesis Example 15

Synthesis of Compound 21

Compound 21 was synthesized in the same way as the method used for Compound 19, with the exception that Compound 18 was substituted with Compound 20.

Mass (nega): 798 (M−K)
Absorption maximum (methanol): 638 nm
Molecular absorption coefficient: 195,000

Synthesis Example 16

Synthesis of Compound 22

The synthesis scheme of Compound 22 is shown below:

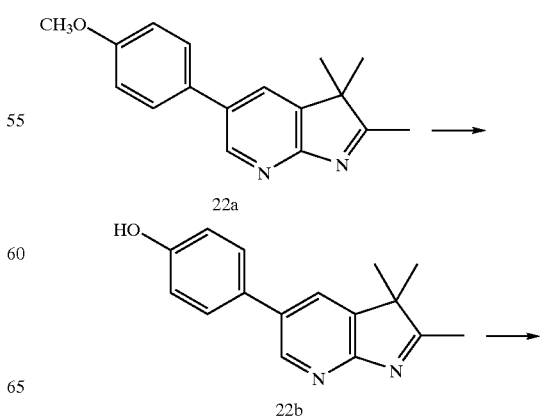

-continued

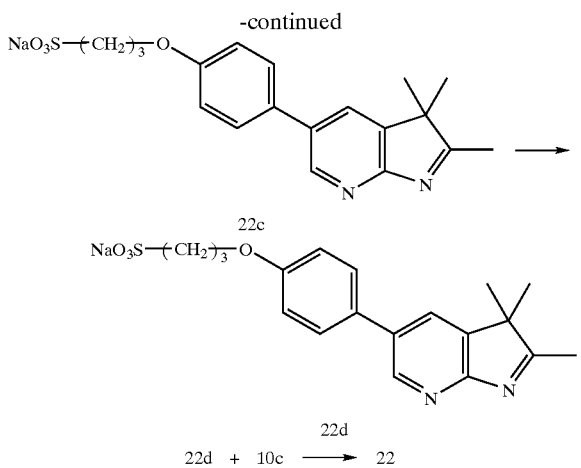

22d + 10c ⟶ 22

(Synthesis of Compound 22b)

Compound 22a (5.0 g, 19 mmol) was dissolved in 47% hydrogen bromide in water (50 ml), and the mixture was heated under reflux for 3 hours. After the reaction solution was cooled to room temperature, water was added thereto to crystallize Compound 22b.
Amount: 3.88 g, Yield: 80%
Mass (posi): 253 (M+H)

(Synthesis of Compound 22c)

Compound 22b (3.0 g, 12 mmol) was dissolved in dimethylformamide (30 ml), and while cooling with ice, 62.5% sodium hydride (0.46 g, 12 mmol) and propanesultone (1.5 g, 12 mmol) were added thereto followed by a reaction for 1 hour. Ethyl acetate and isopropyl alcohol were added to the reaction solution to crystallize Compound 22c.
Amount: 4.4 g, Yield: 93%
Mass (nega): 373 (M−Na)

(Synthesis of Compound 22d)

Compound 22c (3.0 g, 7.6 mmol) was dissolved in dimethylformamide (5 ml), and ethyl 6-bromohexanoate (3.3 g, 15 mmol) was added thereto followed by reaction at 120° C. for 6 hours. In this reaction, alkylation to heterocyclic nitrogen (indole ring part) occurred other than at the target site. However, isopropyl alcohol (5 ml) was added to the reaction solution and the mixture was heated under reflux for 30 minutes, thereby allowing crystallization of only Compound 22d, which was the product of interest where pyridine ring nitrogen is quaternary.
Amount: 2.8 g, Yield: 72%
Mass (posi): 488 (M−Na)

(Synthesis of Compound 22)

Compound 10c (2.79 g, 5 mmol) and Compound 22d (2.6 g, 5 mmol) were dissolved in dimethylformamide (100 ml), and triethylamine (2 ml) was added thereto followed by reaction at 40° C. for 1 hour.

Ethyl acetate (30 ml) was added to the reaction solution to deposit the crude crystal of Compound 22.

The obtained crude crystal was purified by recrystallization from a mixed solvent of methanol and chloroform to obtained Compound 22.
Amount: 1.8 g, Yield: 40%
Mass (nega): 910 (M−Na)
Absorption maximum (methanol): 648 nm
Molecular absorption coefficient: 195,000

Example 1

Synthesis of a Compound 17-dUTP Conjugate 5 mg (2.5 parts) of Compound 17 was dissolved in 0.1M MES buffer (2 ml), then 3.66 mg (5 parts) of WSC hydrochloride and 4.20 mg (5 parts) of Sulfo-NHS were added thereto followed by stirring at room temperature for 15 minutes. After adding thereto 2.2 mg of aminoallyl-dUTP (Sigma) dissolved in 200 μl of 0.1M MES buffer, a reaction was carried out at room temperature for 2 hours. After adding 100 μl of 1M Tris buffer (pH 7.5) and stopping the reaction, the obtained reaction solution was absorbed on a column in which 8 g of ODS silica (YMC-ODS-AQ 120A) was previously filled, and was eluted with 30% methanol solution. After the eluant is concentrated, it was further purified by intermediate pressure preparative chromatography (YAMAZEN Ultrapack ODS-S-40B) to obtain a product of interest with 95% purity (Yield: 71%).
MS analysis value: M-1128

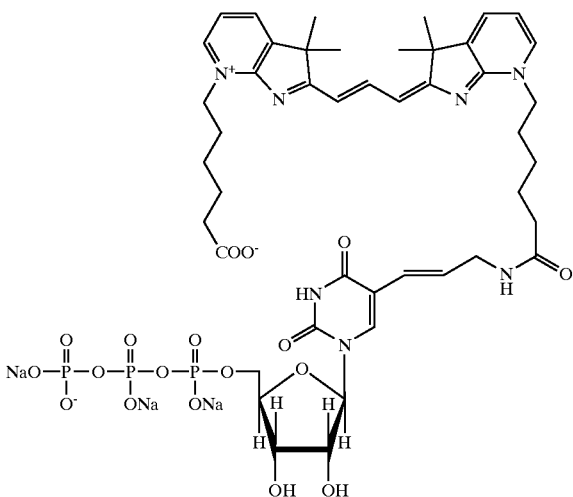

Example 2

Synthesis of a Compound 14-dUTP Conjugate 5.5 mg (2.5 parts) of Compound 14 was dissolved in 200 μl of DMSO, then 3.1 mg (5 parts) of WSC hydrochloride and 3.55 mg (5 parts) of Sulfo-NHS were added thereto followed by stirring at room temperature for 15 minutes. After adding thereto 2.2 mg of aminoallyl-dUTP (Sigma) dissolved in 2 ml of 0.1M MES buffer, a reaction was carried out at room temperature for 2 hours. After adding 100 μl of 1M Tris buffer (pH 7.5) and stopping the reaction, the obtained reaction solution was absorbed on a column in which 8 g of ODS silica (YMC-ODS-AQ 120A) was previously filled, and was eluted with 45% methanol solution. After the eluant is concentrated, it was further purified by intermediate pressure preparative chromatography (YAMAZEN Ultrapack ODS-S-40B) to obtain a product of interest with 94% purity (Yield: 66%).
MS analysis value: M-1206

Example 3

Synthesis of a Compound 1-dUTP Conjugate 6.00 mg (2.5 parts) of Compound 1 was dissolved in 200 μl of DMSO, then 3.1 mg (5 parts) of WSC hydrochloride and 3.55 mg (5 parts) of Sulfo-NHS were added thereto followed by stirring at room temperature for 30 minutes. After adding thereto 2.2 mg of aminoallyl-dUTP (Sigma) dissolved in 2 ml of 0.1M MES buffer, a reaction was carried out at room temperature for 2 hours. After adding 100 μl of 1M Tris buffer (pH 7.5) and stopping the reaction, the obtained reaction solution was absorbed on a column in which 8 g of ODS silica (YMC-ODS-AQ 120A) was previously filled, and was eluted with 50% methanol solution. After the eluant is concentrated, it was further purified by intermediate pressure preparative chromatography (YAMAZEN Ultrapack ODS-S-40B) to obtain a product of interest with 92% purity (Yield: 74%).

MS analysis value: M-1266

Example 4

Synthesis of a Compound 10-dUTP Conjugate 3.27 mg (1.0 part) of Compound 10 was dissolved in 200 $\mu$l of DMSO, then 0.76 mg (1.1 parts) of WSC hydrochloride and 0.86 mg (1.1 parts) of Sulfo-NHS were added thereto followed by stirring at room temperature for 30 minutes. After adding thereto 2.2 mg of aminoallyl-dUTP (Sigma) dissolved in 2 ml of 0.1M MES buffer, a reaction was carried out at room temperature for 2 hours. After adding 100 $\mu$l of 1M Tris buffer (pH 7.5) and stopping the reaction, the obtained reaction solution was absorbed on a column in which 8 g of ODS silica (YMC-ODS-AQ 120A) was previously filled, and was eluted with 40% methanol solution. After the eluant is concentrated, it was further purified by intermediate pressure preparative chromatography (YAMAZEN Ultrapack ODS-S-40B) to obtain a product of interest with 95% purity (Yield: 77%).

MS analysis value: M-1359

Example 5

Synthesis of a Compound 19-dUTP Conjugate 1.00 mg (1.0 part) of Compound 19 was dissolved in 300 $\mu$l of 0.1M MES buffer, then 0.44 mg (2.2 parts) of WSC hydrochloride and 0.50 mg (2.2 parts) of Sulfo-NHS were added thereto followed by stirring at room temperature for 60 minutes. After adding 0.25 mg (0.4 parts) of aminoallyl-dUTP (Sigma) and 300 $\mu$l of 1M carbonate buffer (pH 9.0) thereto, a reaction was carried out at room temperature overnight. After adding 100 $\mu$l of 1M Tris buffer (pH 7.5) and stopping the reaction, the obtained reaction solution was purified by a intermediate pressure preparative chromatography (YAMAZEN Ultrapack ODS-S-40B) to obtain a product of interest with 90% purity (Yield: 62%).

MS analysis value: M-1513

Example 6

Synthesis of a Compound 22-dUTP Conjugate 1.00 mg (1.0 part) of Compound 22 was dissolved in 300 $\mu$l of 0.1M MES buffer, then 0.23 mg (1.1 parts) of WSC hydrochloride and 0.26 mg (1.1 parts) of Sulfo-NHS were added thereto followed by stirring at room temperature for 60 minutes. After adding 0.66 mg (1.0 part) of aminoallyl-dUTP (Sigma) and 300 $\mu$l of 1M carbonate buffer (pH 9.0) thereto, a reaction was carried out at room temperature overnight. After adding 100 $\mu$l of 1M Tris buffer (pH 7.5) and stopping the reaction, the obtained reaction solution was purified by intermediate pressure preparative chromatography (YAMAZEN Ultrapack ODS-S-40B) to obtain a product of interest with 96% purity (Yield: 44%).

MS analysis value: M-1503

Use Example 1

Preparation of Fluorescence-Labeled DNA Probe by Transcription

Human liver mRNA (Clontech) (0.5 $\mu$g) and oligo dT primers (dT$_{18-21}$, Gibco BRL) (0.5 $\mu$g) were mixed, heated at 70° C. for 10 minutes, and quenched on ice. To this mixture, RNaseOUT (Gibco BRL) (40 U), dATP (500 $\mu$M), dGTP (500 $\mu$M), dCTP (500 $\mu$M), dTTP (200 $\mu$M), the Compound 17-dUTP conjugate obtained in Example 1 (100 $\mu$M), SuperScriptII reverse transcriptase (Gibco BRL) (400 U) and DEPC-treated water (to total amount of 20 $\mu$l) were added, and the mixture was reacted at 42° C. for 2 hours. After the reaction, EDTA and NaOH were added thereto and incubated at 65° C. for 1 hour so as to stop the reaction and decompose mRNA. The reaction solution was introduced into CentriSep column (PRINCETON SEPARATION, INC) and unreacted Compound 17-dUTP conjugate or the like were removed to purify the product.

As a control, the reverse transcription reaction was carried out in the same way as stated above using a control fluorescent nucleotide (Cy5-AP3-dUTP; Amersham Pharmacia Biotech) labeled with a dye (Cy5) instead of a Compound 17-dUTP conjugate, and the obtained reaction product was purified.

After the purification, each of the reaction solutions was subjected to agarose gel electrophoresis. The gel was stained with SYBR Green II (Molecular Probes), and was scanned by FLA2000 (Fuji Photo Film Co., Ltd.). As a result, it was found that a more intense and sharper fluorescence was generated with the Compound 17-dUTP conjugate of the present invention than with the control sample.

Furthermore, fluorescence intensity was measured by a fluorometer, and the amount of DNA was measured at an absorbance of 260 nm. From these results, both of the uptake rate and the fluorescence intensity per 1 $\mu$M of the probe were calculated. The results are shown in Table 1. As shown in Table 1, in the case where the Compound 17-dUTP conjugate of the present invention was used, both of the uptake rate and the fluorescence intensity were higher.

TABLE 1

| Fluorescent Dye | Uptake Rate (Dye/1 kb) | Fluorescence Intensity (/$\mu$M) |
|---|---|---|
| Compound 17-dUTP Conjugate | 4 | 5,000 |
| Cy5-AP3-dUTP (control sample) | 2 | 1,000 |

Use Example 2

Preparation of a Fluorescent Dye-Labeled DNA Probe by PCR

Composition of PCR Reaction Solution:
Template DNA: 10 pg
Primers 1 and 2: 0.5 $\mu$M each
dATP, dGTP, dCTP: 200 $\mu$M each
dTTP: 150 $\mu$M each
Compound 17-dUTP conjugate or Cy5-AP3-dUTP: 50 $\mu$M
Pyrobest DNA polymerase (TAKARA): 0.5 units
Distilled water: to total amount of 20 $\mu$l
Note: As a template DNA, pCR-Script™ SK(+) (STRATAGENE) into which $\alpha$-2-HS-glycoprotein gene was integrated, was used, and each sequence of primers 1 and 2 was respectively tggccgcctt caacgctcag (SEQ ID NO: 1 in the sequence listing) and tcaggcactt tcattaacag gcacat (SEQ ID NO: 2 in the sequence listing).

Using the solution of the above composition as a PCR reaction solution, a cycle of 94° C. for 30 seconds, 60° C. for 30 seconds and 72° C. for 30 seconds was repeated 30 times for the PCR reaction. The reaction solution was transferred to a CentriSep column (PRINCETON SEPARATION, INC), and unreacted fluorescent nucleotides and the like were removed to purify the product. After purification, the reaction solution was subjected to agarose gel electrophoresis. The gel was stained with SYBR Green II (Molecular Probes) and was scanned by FLA2000 (Fuji Photo Film Co., Ltd.). As a result, it was found that more intense and sharper fluorescence was generated with the Compound 17-dUTP conjugate of the present invention than with the control sample.

Furthermore, fluorescence intensity was measured by a fluorometer, and the amount of DNA was measured at an absorbance of 260 nm. From these results, both of the uptake rate and the fluorescence intensity per 1 $\mu$M of the probe were calculated. The results are shown in Table 2. As shown in Table 2, in the case where the Compound 17-dUTP conjugate of the present invention was used, both of the uptake rate and the fluorescence intensity were higher.

TABLE 2

| Fluorescent Dye | Uptake Rate (Dye/1 kb) | Fluorescence Intensity (/$\mu$M) |
|---|---|---|
| Compound 17-dUTP Conjugate | 30 | 5,000 |
| Cy5-AP3-dUTP (control sample) | 10 | 1,000 |

Example 7

Synthesis of a Streptavidin-Compound 1 Conjugate

1. Activation of Fluorescent Dye

To 100 $\mu$l of DMSO solution containing 24 mg/ml of Compound 1 were successively added 31 $\mu$l of DMSO solution containing 48 mg/ml of WSC (Wako Pure Chemical Industries, Ltd.) and 36 $\mu$l of DMSO solution containing 48 mg/ml of sufoNHS (Dojin Do Laboratories), and the mixture was stirred at room temperature for 1 hour.

2. Synthesis of a Streptavidin-Compound 1 Conjugate

To 300 $\mu$l of 100 nM carbonate buffer (pH 8.3) containing 4 mg/ml of streptavidin (Wako Pure Chemical Industries, Ltd.) was added 83 $\mu$l of the above-prepared activated form of the fluorescent dye (Compound 1), and the mixture was stirred at room temperature for 1 hour. This reaction solution was subjected to gel filtration using 100 mM phosphate buffer (pH 7.5) of NAP25 (Pharmacia) to remove unreacted fluorescent dye.

Example 8

Synthesis of a Streptavidin-Compound 10 Conjugate

1. Activation of Fluorescent Dye

To 100 $\mu$l of DMSO solution containing 24 mg/ml of Compound 10 were successively added 29 $\mu$l of DMSO solution containing 48 mg/ml of WSC (Wako Pure Chemical Industries, Ltd.) and 33 $\mu$l of DMSO solution containing 48 mg/ml sufoNHS (Dojin Chemicals, Co.), and the mixture was stirred at room temperature for 1 hour.

2. Synthesis of Streptavidin and Fluorescent Dye

To 300 $\mu$l of 100 nM carbonate buffer (pH 8.3) containing 4 mg/ml of streptavidin (Wako Pure Chemical Industries, Ltd.) was added 83 $\mu$l of the above-prepared activated form of the fluorescent dye (compound 10), and the mixture was stirred at room temperature for 1 hour. This reaction solution was subjected to gel filtration using 100 mM phosphate buffer (pH 7.5) of NAP25 (Pharmacia) to remove unreacted fluorescent dye.

Example 9

Synthesis of a Streptavidin-Compound 14 Conjugate

1. Activation of Fluorescent Dye

To 100 $\mu$l of DMSO solution containing 12 mg/ml of Compound 14 were successively added 16 $\mu$l of DMSO solution containing 48 mg/ml WSC (Wako Pure Chemical Industries, Ltd.) and 17 $\mu$l of DMSO solution containing 48 mg/ml of sufoNHS (Dojin Chemicals Co.), and the mixture was stirred at room temperature for 1 hour.

2. Synthesis of Streptavidin and Fluorescent Dye

To 150 $\mu$l of 100 nM carbonate buffer (pH 8.3) containing 4 mg/ml of streptavidin (Wako Pure Chemical Industries, Ltd.) was added 40 $\mu$l of the above-prepared activated form of the fluorescent dye (Compound 14), and the mixture was stirred at room temperature for 1 hour. This reaction solution was subjected to gel filtration using 100 mM phosphate buffer (pH 7.5) of NAP25 (Pharmacia) to remove unreacted fluorescent dye.

Example 10

Confirmation of a Streptavidin-Fluorescent Dye Conjugate

Using the streptavidin-Compound 14 conjugate synthesized in Example 9, the conjugation of streptavidin to Compound 14 was confirmed as follows.

Spreptoavidin (2.5 $\mu$g), a streptavidin-Compound 14 conjugate (3.6 $\mu$g) and a molecular weight marker (1.7 $\mu$g) were subjected to SDS-PAGE electrophoresis in accordance with standard techniques. The gel was scanned by FLA2000 (Fuji Photo Film Co., Ltd.) to measure fluorescence. As a result, in the lane where the streptavidin-Compound 14 conjugate was electrophoresed, fluorescent bands were detected at the positions of about 15 kDa and about 30 kDa. It is known that spreptoavidin is a tetrameric protein where 4 subunits are assembled and has a molecular weight of about 60 kDa. It is considered that each of about 15 kDa and about 30 kDa bands, detected as above, respectively correspond to monomeric and dimeric subunits.

The same gel was stained with cyproorange to detect protein. As a result, in the lane of a streptavidin-Compound 14 conjugate, fluorescent bands were detected at the positions of about 15 kDa and about 30 kDa.

From the above results, it is found that a streptavidin-Compound 14 conjugate which is fluorescent was synthesized.

Use Example 3

Each of 2- to 512-fold diluted solutions (1 $\mu$l) obtained by diluting various biotin-labeled PCR products (20, 200, 500, 1,000 and 1,500bp (40 ng/ml each)) encoding $\alpha$-2-HS-glycoprotein was spotted to a nylon membrane (Hybond/Amersham pharmacia), air-dried, and UV-crosslinked. The membrane was washed and blocked with DIGWash and Block Set (Roche). Then, the membrane was impregnated with avidin-fluorescent dye (protein concentration: 3 $\mu$g/ml) which was prepared in Example 7, and was left at room temperature for 30 minutes. After washing with the above washing solution, the membrane was scanned by FLA2000 (Fuji Photo Film Co., Ltd.) to measure the fluorescence.

The results are shown in FIG. 1.

As shown in FIG. 1, fluorescent intensity dependent on the amount of the target nucleic acid (PCR product), was observed. From use example 3, it was confirmed that the use of the fluorescent streptavidin of the present invention enables detection and quantification of the target substance.

Industrial Applicability

The fluorescent nucleotide of the present invention is a novel substance. Since both of its uptake rate during DNA synthesis and its fluorescence intensity after uptake are excellent, it is useful as a labeling substance for nucleic acids. The fluorescent avidin of the present invention is a novel substance, and is useful as a reagent for analyzing biological components such as nucleic acids, proteins or sugars.

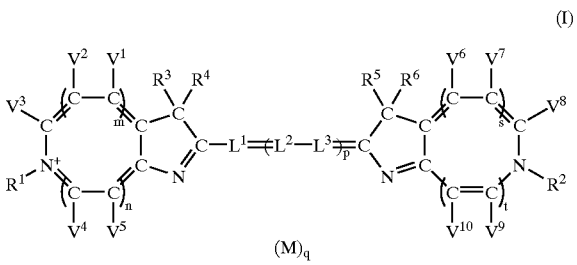

(I)

wherein $R^1$ and $R^2$ each independently represent an alkyl group that may be substituted with a reactive group capable of covalently bonding to A-B-; $R^3$, $R^4$, $R^5$, and $R^6$ each independently represent an alkyl

What is claimed is:

1. A fluorescent substance which is represented by a formula: A-B-C wherein

A is a residue of natural or synthetic nucleotide, oligonucleotide, polynucleotide and possesses a base moiety capable of binding to a divalent linking group or a single bond and binds to B at the base moiety in said residue, or A is a residue of avidin or streptavidin;

B is a divalent linking group or a single bond; and

C is a monovalent group derived from a general formula (I) and binds to B at a reactive group present in $R^1$ or $R^2$:

group, and $R^3$ and $R^4$, an/or $R^5$ and $R^6$ may bind to each other to form a saturated carbon-ring together with a carbon atom(s) to which they bind; $V^1$, $V^2$, $V^3$, $V^4$, $V^5$, $V^6$, $V^7$, $V^8$, $V^9$ and $V^{10}$ each independently represent a hydrogen atom or a monovalent substituent, and two adjacent groups thereof may bind to form a ring; L1, L2, and L3 represent a substituted or unsubstituted methane group; each of M, n, s, and t represents 0 or 1, provided that m+n=1 and s+t=1; p represents 1, 2, or 3; M represents a counter ion; and q represents a number required to neutralize the charge of a molecule.

2. The fluorescent substance according to claim 1, wherein at least one of $R^1$ and $R^2$ is an alkyl group substituted with an active ester group capable of covalently bonding to an amino group, a hydroxyl group or a thiol group which is present in the group represented by A-B-.

3. The fluorescent substance according to claim 1, wherein at least one of $R^1$ and $R^2$ is an alkyl group substituted with a carboxyl group.

4. The fluorescent substance according to claim 1, wherein A is a residue of natural or synthetic nucleotide, oligonucleotide, or polynucleotide.

5. The fluorescent substance according to claim 1, wherein A is a residue of nucleotide.

6. The fluorescent substance according to claim 1, wherein A is a residue of natural or synthetic nucleotide which are selected from the group consisting of: (1) nucleotides consisting of AMP, ADP, ATP, GMP, GDB, GTP, CMP, CDP, CTP, UMP, UDP, UTP, TMP, TDP, TTP, 2-Me-AMP, 2-Me-ADP, 2-Me-ATP, 1-Me-GMP, 1Me-GDP, 1-Me-GTP, 5Me-CMP, 5-Me-CDP, 5-Me-CTP, 5-MeO-CMP, 5-MeO-CDP, AND 5-MeO-CTP; (2) deoxynucleotides and dideoxynucleotides corresponding to said nuleotides; and (3) derivatives derived from said nucleotides as described in (1) and (2).

7. The fluorescent substance according to claim 1, wherein A is a residue of avidin or streptavidin.

8. The fluorescent substance according to claim 1, wherein B is a linking group selected from —CH$_2$—, —CH=CH—, —C, C—, —CO—, —O—, —S—, —NH— or combinations thereof, wherein a hydrogen atom on the linking group may be further substituted with a substituent.

9. The fluorescent substance according to claim 1, wherein B is an aminoallyl group.

10. A process of preparing fluorescence-labeled nucleic acids which comprises the step of conducting a reaction of the synthesis of nucleic acid by using nucleic acid synthetase, a nucleic acid as a template, and the fluorescent substance according to claim 4.

11. The method according to claim 10, wherein the reaction of the synthesis of nucleic acid is a reaction selected from the group consisting of a reverse transcription reaction, a terminal transferase reaction, a random prime method, a PCR method, and a nick-translation method.

12. A nucleic acid probe or primer which is labeled with the fluorescent substance according to claim 4.

13. A diagnostic agent or a reagent for detecting nucleic acids, which comprises the fluorescent substance according to claim 4.

14. A kit for detecting nucleic acids, which comprises (1) the fluorescent substance according to claim 4, (2) a nucleic acid synthetase, and (3) a buffer.

15. An analytical reagent or a diagnostic agent consisting of the fluorescent substance according to claim 7.

16. An analytical kit, which comprises (1) the fluorescent substance according to claim 7, and (2) biotin or a biotin-labeled substance.

* * * * *

UNITED STATES PATENT AND TRADEMARK OFFICE
CERTIFICATE OF CORRECTION

PATENT NO. : 6,642,375 B2
DATED : November 4, 2003
INVENTOR(S) : Hiroko Inomata

It is certified that error appears in the above-identified patent and that said Letters Patent is hereby corrected as shown below:

Title page,
Item [30] Foreign Application Priority Data, is omitted
please insert -- JP 11-347886 December 7, 1999
               JP 11-348015 December 7, 1999 --

Signed and Sealed this

Twenty-seventh Day of July, 2004

JON W. DUDAS
*Acting Director of the United States Patent and Trademark Office*